(12) United States Patent
Schultheiss et al.

(10) Patent No.: US 10,465,204 B2
(45) Date of Patent: Nov. 5, 2019

(54) FUNGAL RESISTANT PLANTS EXPRESSING MYBTF

(71) Applicant: BASF PLANT SCIENCE COMPANY GMBH, Ludwigshafen (DE)

(72) Inventors: Holger Schultheiss, Boehl-Iggelheim (DE); Ralf Flachmann, Limburgerhof (DE); Tobias Mentzel, Roemerberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 14/772,140

(22) PCT Filed: Mar. 7, 2014

(86) PCT No.: PCT/EP2014/054461
§ 371 (c)(1),
(2) Date: Sep. 2, 2015

(87) PCT Pub. No.: WO2014/135682
PCT Pub. Date: Sep. 12, 2014

(65) Prior Publication Data
US 2016/0068856 A1    Mar. 10, 2016

(30) Foreign Application Priority Data
Mar. 8, 2013    (EP) .................................. 13158321

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS 8,030,546 B2 * 10/2011 Reuber ................ C07K 14/415
435/419
2009/0144849 A1    6/2009 Lutfiyya
2012/0137382 A1    5/2012 Repetti

FOREIGN PATENT DOCUMENTS

| CN | 102010466 A | 4/2011 |
|---|---|---|
| CN | 102161697 A | 8/2011 |
| CN | 102676544 A | 9/2012 |
| CN | 102864169 A | 1/2013 |
| WO | WO-2006/130156 A2 | 12/2006 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/149804 A1 | 10/2013 |
| WO | WO-2013/152917 A1 | 10/2013 |
| WO | WO-2014/024079 A2 | 2/2014 |
| WO | WO-2014/024090 A2 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/076659 A1 | 5/2014 |
| WO | WO-2014/117988 A1 | 8/2014 |
| WO | WO-2014/117990 A1 | 8/2014 |
| WO | WO-2014/118018 A1 | 8/2014 |
| WO | WO-2014/135682 A1 | 9/2014 |

OTHER PUBLICATIONS

Friedberg. Bioinformatics. 7: 225-242, 2006.*
Hill et al. Biochem. Biophys. Res. Comm. 244:573-577, 1998.*
Guo et a.Proc. Natl. Acad. Sci. USA 101:9205-9210, 2004.*
Fourgoux-Nicol et al.Plant Molecular Biology 40: 857-872, 1999.*
Goellner et al (Molecular Plant Pathology (2010), vol. 11(2), pp. 169-177).*
Dubos et al., "MYB transcription factors in *Arabidopsis*", *Trends in Plant Science*, 15(10):573-581 (2010).
European Search Report in EP 13 15 8321 dated Jul. 10, 2013.
Godoy et al., "Diagrammatic scale for assessment of soybean rust severity", *Fitopatol. Bras.*, 31(1):63-8 (2006).
Heath, "Cellular interactions between biotrophic fungal pathogens and host or nonhost plants", *Can. J. Plant Pathol.*, 24:259-64 (2002).
International Search Report and Written Opinion in PCT/EP2014/054461 dated May 14, 2014.
Kawalleck et al., "Polyubiquitin gene expression and structural properties of the ubi4-2 gene in *Petroselinum crispum*", *Plant Mol. Biol.*, 21:673-84 (1993).
Neu et al., "Cytological and molecular analysis of the *Hordeum vulgare-Puccinia triticina* nonhost interaction", *MPMI*, 16(7):626-33 (2003).
Choi et al., Expression patterns in soybean resistant to Phakopsora pachyrhizi reveal the importance of peroxidases and lipoxygenases, Funct. Integr. Genomics, 8(4):341-59 (2008).
Pandey et al., Functional analysis of the Asian soybean rust resistance pathway mediated by Rpp2, Mol. Plant Microbe Interact., 24(2):194-206 (2011).

* cited by examiner

*Primary Examiner* — Medina A Ibrahim
(74) *Attorney, Agent, or Firm* — Marshall, Gerstein & Borun LLP

(57) ABSTRACT

The present invention relates to a method of increasing resistance against fungal pathogens of the order Pucciniales in plants and/or plant cells. This is achieved by increasing the expression of a MybTF protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the order Pucciniales, and to recombinant expression vectors comprising a sequence that is identical or homologous to a sequence encoding a MybTF protein.

21 Claims, 9 Drawing Sheets

Figure 1:
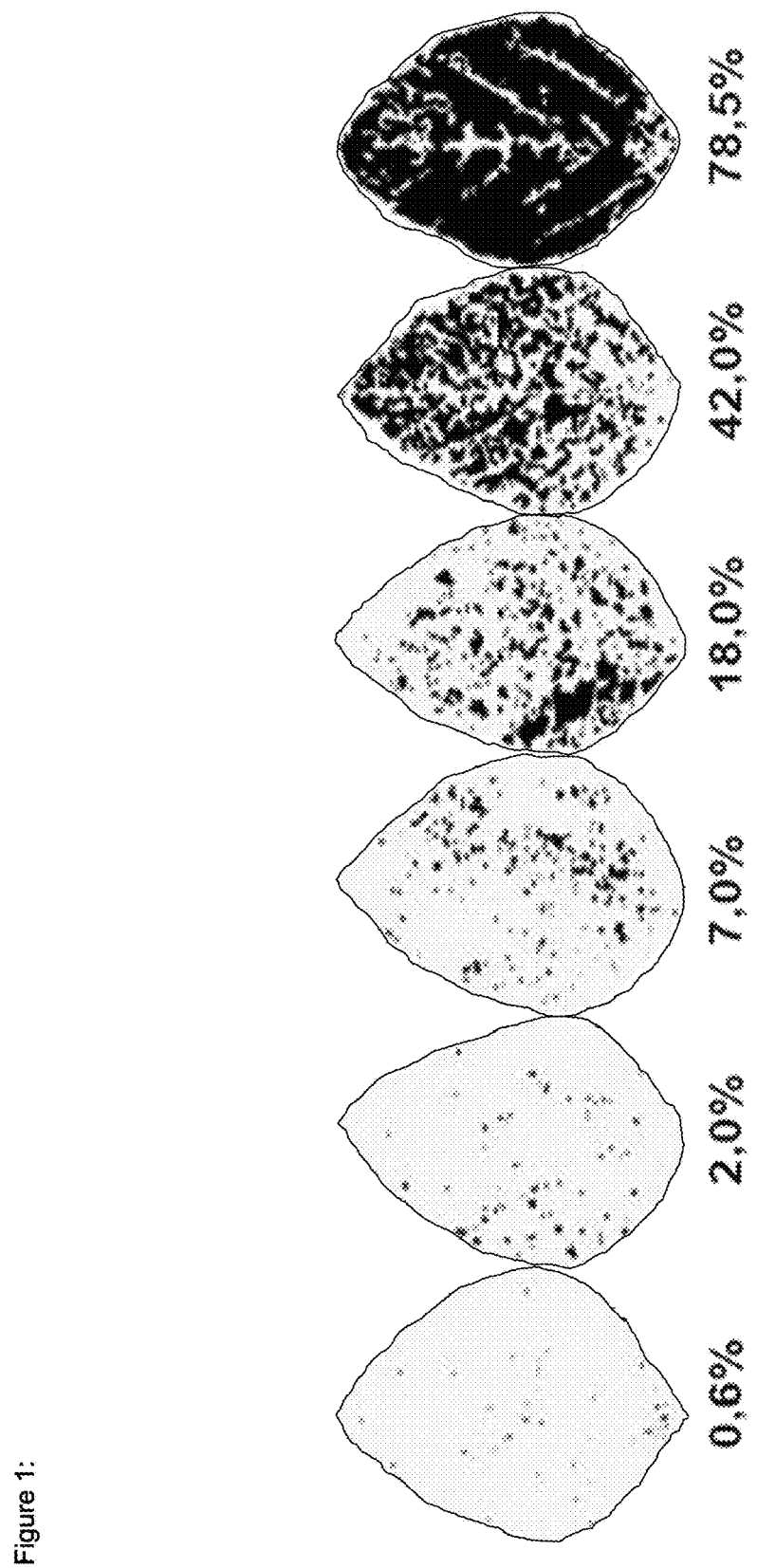

Specification includes a Sequence Listing.

Figure 3:

```
                         1  GTATATATGAGACATTAGTTATAGAAGAGAGACTAAC
At3g29020-genomic    (1)                                      ATGGATGGATTTTCATGTTT   60
      MybTF-DNA     (1)  ------------------------------------ATGAAGATGGATTTTCATGTT
    At3g29020.2-CDS (1)  ------------------------------------ATGAAGATGGATTTTCATGTT
    At3g20020.1-CDS (1)  ------------------------------------ATGGATTTTCATGTTT 61  CCAAGAATACCCTTTTGAGTTTCATTGCAAGGAACACATTTAATTGGTTTAGACAAAA  120
At3g29020-genomic   (61)  CCAAGAATACCCTTTTGAGTTTCATTGCAAGGAACACATTTAATTGGTTTAGACAAAA
      MybTF-DNA    (24)  CCAAGAATACCCTTTTGAGTTTCATTGCAAGGAACACATTTAATTGGTTTAGACAAAA
    At3g29020.2-CDS (24)  CCAAGAATACCCTTTTGAGTTTCATTGCAAGGAACACATTTAATTGGTTTAGACAAAA
    At3g20020.1-CDS (18)  CCAAGAATACCCTTTTGAGTTTCATTGCAAGGAACACATTTAATTGGTTTAGACAAAA 121                                                             180
At3g29020-genomic  (121)  CAATGCAGTGTCTGAAACAGTAGAACAGTTCTGTAATATAAAGAAGATGCAGAAGAAGAG
      MybTF-DNA    (84)  CAATGCAGTGTCTGAAACAGTAGAACAGTTCTGTAATATAAAGAAGATGCAGAAGAAGAG
    At3g29020.2-CDS (84)  CAATGCAGTGTCTGAAACAGTAGAACAGTTCTGTAATATAAAGAAGATGCAGAAGAAGAG
    At3g20020.1-CDS (78)  CAATGCAGTGTCTGAAACAGTAGAACAGTTCTGTAATATAAAGAAGATGCAGAAGAAGAG 181                                                             240
At3g29020-genomic  (181)  TGATGATTTGAAGCTTAGATGAGGAAGAAGAGAGTCGAGTAGTGGTTGCTAGCCGTAGCGG
      MybTF-DNA   (144)  TGATGATTTGAAGCTTAGATGAGGAAGAAGAGAGTCGAGTAGTGGTTGCTAGCCGTAGCGG
    At3g29020.2-CDS (144)  TGATGATTTGAAGCTTAGATGAGGAAGAAGAGAGTCGAGTAGTGGTTGCTAGCCGTAGAGG
    At3g20020.1-CDS (138)  TGATGATTTGAAGCTTAGATGAGGAAGAAGAGAGTCGAGTAGTGGTTGCTAGCCGTAGCGG 241                                                             300
At3g29020-genomic  (241)  ACATTGGAGGATCTCTGAAATATCTCAGCTTATGCAGCTTGTTCCGTTTACGGTCCTCA
      MybTF-DNA   (204)  ACATTGGAGGATCTCTGAAGATATCTCAGCTTATGCAGCTTGTTCCGTTTACGGTCCTCA
    At3g29020.2-CDS (204)  ACATTGGAGGATCTCTGAAGATATCTCAGCTTATGCAGCTTGTTCCGTTTACGGTCCTCA
    At3g20020.1-CDS (198)  ACATTGGAGGATCTCTGAGATATCTCAGCTTATGCAGCTTGTTCCGTTTACGGTCCTCA 301                                                             360
At3g29020-genomic  (301)  AAACTGGAACCACATTGCCCTTAGCTAATTGCCGGAAGGAAGAACATGGAACAGTTGAAA
      MybTF-DNA   (264)  AAACTGGAACCACATTGCCCTTAGCTAATTGCCGGAAGGAAGAACATGGAACAGATAGAG
    At3g29020.2-CDS (264)  AAACTGGAACCACATTGCCCTTAGCTAATTGCCGGAAGGAAGAACATGGAACAG
    At3g20020.1-CDS (258)  AAACTGGAACCACATTGCCCTTAGCTAATTGCCGGAAGGAAGAACATGGAACAG 361                                                             420
At3g29020-genomic  (361)  TGTTAATCTTCCCTTAGCTAATTGCCGGAAGCTAATTCCCGGAAGAACATGGAATGTTTC
      MybTF-DNA   (324)  TGTTAATCTTCCCTTAGCTAATTGCCGGAAGCTAATTCCCGGAAGAACATGGAATGTTTC
    At3g29020.2-CDS (305)  ------------------------------------------------
    At3g20020.1-CDS (299)  ------------------------------------------------
```

Figure 3 (continued):

```
At3g29020-genomic  (421) TTTGTGTTTTGTCTTAAGCAAGACTGCTCGATTGCGTCGTTTACCAGTTAGATCCG  480
       MybTF-DNA   (384) TTTGTGTTTTGTCTTAAGAAAGAGCTGCAGATTGAGTCGTTGGTTAACAGTTAGATCCG
    At3g29020.2-CDS (305) ------------------CAAACAGCTGCAGATTGAGTCGTTGGTTAACAGTTAGTCCG
    At3g20020.1-CDS (299) ------------------CAAACAGCTGCAGATTGAGTCGTTGGTTAACCAGTTAGTCCG At3g29020-genomic  (481) AGGATTAACAAGAGAGCTTCAGTGATGATGAAGAAGAAGAAGAAGAAGACTACTTGCTCTATAGA  540
       MybTF-DNA   (444) AGGATTAACAAGAGAGCTTCAGTGATGATGAAGAAGAAGAAGAAGAAGACTACTTGCTCTATAGA
    At3g29020.2-CDS (346) AGGATTAACAAGAGAGCTTCAGTGATGATGAAGAAGAAGAAGAAGAAGACTACTTGCTCTATAGA
    At3g20020.1-CDS (340) AGGATTAACAAGAGAGCTTCAGTGATGATGAAGAAGAAGAAGAAGAGAGAGACTGCTGCTCTATAGA At3g29020-genomic  (541) GCTTTTGGTAACAAATGGGCTATGATTGCTAAGCTTTCAATGGAGGAACAGAGATAATGCC  600
       MybTF-DNA   (504) GCTTTTGGTAACAAATGGGCTATGATTGCTAAGCTTTCAATGGAGGAACAGAGATAATGCC
    At3g29020.2-CDS (406) GCTTTTGGTAACAAATGGGCTATGATTGCTAAGCTTTCAATGGAGGAACAGAGATAATGCC
    At3g20020.1-CDS (400) GCTTTTGGTAACAATGGGCTATGATTGCTAAGCTTTCAATGGAGGAACAGAGATAATGCC At3g29020-genomic  (601) TTGAAGAATCATTGGCATGTTCTCATGTTCTGCTCCAAGATGAGACAGCAATCAAGTTCTTAC  660
       MybTF-DNA   (564) TTGAAGAATCATTGGCATGTTCTCATGTTCTGCTCCAAGATGAGACAGCAATCAAGTTCTTAC
    At3g29020.2-CDS (466) TTGAAGAATCATTGGCATGTTCTCATGTTCTGCTCCAAGATGAGACAGCAATCAAGTTCTTAC
    At3g20020.1-CDS (460) TTGAAGAATCATTGGCATGTTCTCATGTTCTGCTCCAAGATGAGACAGCAATCAAGTTCTTAC At3g29020-genomic  (661) GTCCAAGATTCAATGGTTCTGCTCCTTGTCCATCGATTCTAACAGATCTAACAGCAAAATCTCAATCTT  720
       MybTF-DNA   (624) GTCCAAGATTCAATGGTTCTGCTCCTTGTCCATCGATTCTAACAGATCTAACAGCAAAATCTCAATCTT
    At3g29020.2-CDS (526) GTCCAAGATTCAATGGTTCTGCTCCTTGTCCATCGATTCTAACAGATCTAACAGCAAAATCTCAATCTT
    At3g20020.1-CDS (520) GTCCAAGATTCAATGGTTCTGCTCCTTGTCCATCGATTCTAACAGATCTCAACAGCAAAATCTCAATCTT At3g29020-genomic  (721) TCTCCTGGTTTGTCTGTCTCGTTTGTCTGCTTACCTTACAACAATCAATTGCATTACTTGTATTGTA  780
       MybTF-DNA   (684) TCTCCTGGTTTGTCTGTCTCGTTTGTCTGCTTACCTTACAACAATCAATTGCATTACTTGTATTGTA
    At3g29020.2-CDS (586) TCTCCTG-----------------------------------------------------------
    At3g20020.1-CDS (580) TCTCCTGGTTTGTCTGTCTCGTTTGTCTGCTTACCTTACAACAATCAATTGCATTACTTGTATTGTA At3g29020-genomic  (781) ATGAGATTACTTTCGATATTTATCACTCAGGAACAATGAACTTATGGTTTGGTTTCAAAAG  840
       MybTF-DNA   (744) ATGAGATTACTTTCGATATTTATCACTCAGGAACAATGAACTTATGGTTTGGTTTCAAAAG
    At3g29020.2-CDS (593) ------------------------------------------------------------
    At3g20020.1-CDS (640) ATGAGATTACTTTCGATATTTATCACTCAGGAACAATGAACTTATGGTTTGGTTTCAAAAG
```

Figure 3 (continued):

Figure 3 (continued):

```
At3g29020-genomic  (1261) TGCTTACTCCTGTCATTATTATCAAAGTCTCTGACTTTTCTTTTGTTAGCCATTAACATG  1320
        MybTF-DNA  (1188) ------------------------------------------------------------
     At3g29020.2-CDS (919) ------------------------------------------------------------
     At3g20020.1-CDS (703) ------------------------------------------------------------

1321                    1340
At3g29020-genomic  (1321) ACAAGCTAAAGACATCAAGT
        MybTF-DNA  (1188) --------------------
     At3g29020.2-CDS (919) --------------------
     At3g20020.1-CDS (703) --------------------
```

Figure 4:

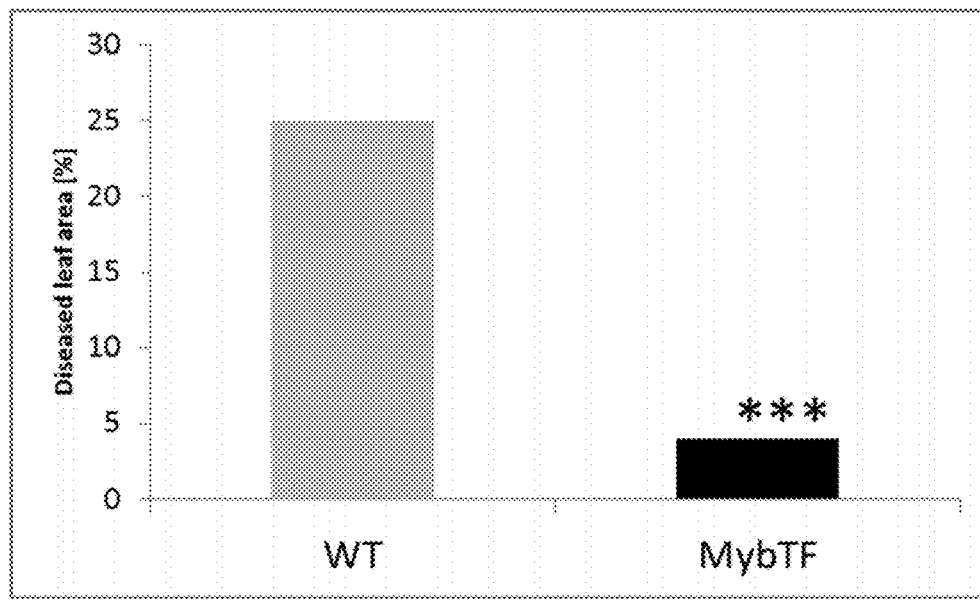

Figure 5:

| SEQ ID NO: | Description of the sequence listing |
|---|---|
| 1 | Nucleotide sequence of the MybTF gene; Arabidopsis thaliana |
| 2 | Nucleotide sequence of the optimized coding sequence CDS1 of the MybTF gene, which is codon optimized for optimal expression in soybean (Glycine max) |
| 3 | Nucleotide sequence of the optimized coding sequence CDS2 of the MybTF gene, which is codon optimized for optimal expression in soybean (Glycine max) |
| 4 | Nucleotide sequence of the second CDS (CDS2) sequence (At3g29020.2, TAIR accession No 4010715313) of the MybTF gene derived from the genomic sequence; Arabidopsis thaliana |
| 5 | Amino acid sequence of the MybTF protein as derived from CDS2 nucleotide sequence, Arabidopsis thaliana |
| 6 | Nucleotide sequence of the first CDS (CDS1) sequence (At3g29020.1, accession No NM_113823) of the MybTF gene derived from the genomic sequence; Arabidopsis thaliana; |

Figure 5 continued:

| 7 | Amino acid sequence of the MybTF protein as derived from CDS1 nucleotide sequence, Arabidopsis thaliana |
|---|---|
| 8 | Nucleotide sequence of the full-length genomic MybTF sequence (TAIR accession No 4010724011) |
| 9 | Nucleotide sequence MybTF, variant 1 |
| 10 | Nucleotide sequence MybTF, variant 2 |
| 11 | Nucleotide sequence MybTF, variant 3 |
| 12 | Nucleotide sequence MybTF, variant 4 |
| 13 | Nucleotide sequence MybTF, variant 5 |
| 14 | Nucleotide sequence MybTF, variant 6 |
| 15 | Nucleotide sequence MybTF, variant 7 |
| 16 | Nucleotide sequence MybTF, variant 8 |
| 17 | Nucleotide sequence MybTF, variant 9 |
| 18 | Nucleotide sequence MybTF, variant 10 |
| 19 | Nucleotide sequence MybTF, variant 11 |
| 20 | Nucleotide sequence MybTF, variant 12 |
| 21 | Nucleotide sequence MybTF, variant 13 |
| 22 | Nucleotide sequence MybTF, variant 14 |
| 23 | Nucleotide sequence MybTF, variant 15 |
| 24 | Nucleotide sequence MybTF, variant 16 |
| 25 | Nucleotide sequence MybTF, variant 17 |
| 26 | Amino acid sequence MybTF, variant 17 |
| 27 | Nucleotide sequence MybTF, variant 18 |
| 28 | Amino acid sequence MybTF, variant 18 |
| 29 | Nucleotide sequence MybTF, variant 19 |
| 30 | Amino acid sequence MybTF, variant 19 |
| 31 | Nucleotide sequence MybTF, variant 20 |
| 32 | Amino acid sequence MybTF, variant 20 |
| 33 | Nucleotide sequence MybTF, variant 21 |
| 34 | Amino acid sequence MybTF, variant 21 |
| 35 | Nucleotide sequence MybTF, variant 22 |
| 36 | Amino acid sequence MybTF, variant 22 |
| 37 | Nucleotide sequence MybTF, variant 23 |
| 38 | Amino acid sequence MybTF, variant 23 |
| 39 | Nucleotide sequence MybTF, variant 24 |
| 40 | Amino acid sequence MybTF, variant 24 |
| 41 | Nucleotide sequence MybTF, variant 25 |
| 42 | Amino acid sequence MybTF, variant 25 |

Figure 5 continued:

| 43 | Nucleotide sequence MybTF, variant 26 |
|---|---|
| 44 | Amino acid sequence MybTF, variant 26 |
| 45 | Nucleotide sequence MybTF, variant 27 |
| 46 | Amino acid sequence MybTF, variant 27 |
| 47 | Nucleotide sequence MybTF, variant 28 |
| 48 | Amino acid sequence MybTF, variant 28 |
| 49 | Nucleotide sequence MybTF, variant 29 |
| 50 | Amino acid sequence MybTF, variant 29 |
| 51 | Nucleotide sequence MybTF, variant 30 |
| 52 | Amino acid sequence MybTF, variant 30 |
| 53 | Nucleotide sequence MybTF, variant 31 |
| 54 | Amino acid sequence MybTF, variant 31 |
| 55 | Nucleotide sequence MybTF, variant 32 |
| 56 | Amino acid sequence MybTF, variant 32 |

SEQUENCE LISTING

```
<160> NUMBER OF SEQ ID NOS: 56

<210> SEQ ID NO 1
<211> LENGTH: 1187
<212> TYPE: DNA
<213> ORGANISM: Arabidopsis thaliana
<220> FEATURE:
<221> NAME/KEY: misc_feature
<222> LOCATION: (1)..(1187)
<223> OTHER INFORMATION: Nucleotide sequence of the MybTF gene;
      mol_type = unassigned DNA

<400> SEQUENCE: 1
atgaagatgg attttcatg tttccaagaa tacccttttg agtttcattg cagaggaaca      60
acatttaatg ggtttagaga aaacaatgca gtgtctgaaa cagtagaaga gttctgtaat     120
aaaagaagga tgcagaagaa gagtgatgat ttgaaaacta agaagaagaa gaaacagagt     180
```

```
gtttctaggg tttgtagtag aggacattgg aggatctctg aagatactca gcttatggag    240
cttgtttcgg tttacggtcc tcaaaactgg aaccacattg cagagagtat gcaaggaaga    300
acaggtaacg acaaaaattg aaatctttaa tcttccctta gctaattccg aacatgaaa     360 cttacaatgt ttttcttgc ttctttgtgt tttgtcttaa aggaaagagc tgcagattga    420
ggtggtttaa ccagttagat ccgaggatta acaagagagc tttcagtgat gaagaagaag    480
agagactact tgctgctcat agagcttttg gtaacaaatg gctatgatt gctaagcttt     540 tcaatggaag aacagataat gccttgaaga atcattggca tgttctcatg caaggaaga    600 tgagacagca atcaagttct tacgtccaaa gattcaatgg ttctgctcat gaatctaaca    660
cagatcacaa aatcttcaat ctttctcctg gtttgtctct tcttaccta cacatatgca    720 ttgagtttaa ctctgttatt gtaatgagat actttcgata tttatcactc aggaacaatg    780
aacttatggt ttggtcacaa aagtagtcag attgcaagtt tggtgagtct ttaagtttca    840
tggttctgtg tgttcttgca ggtaatgtag atgatgatga agatgtgaat ctgaaaaagt    900
gcagctggga aatgctaaaa gagggaacta ctaacctgaa agctcagtat ctccaagaag    960
aatatagttc ttcacgcatg ccgatgcagg gtccacatca tcactactca accttccctg    1020
cagattcctt ggcactgaca ctgcatgtct ccatccagga accatcatca tcatcgtcat    1080
tatcactgcc atcatcatca acaactggag aacatacaat ggtgaccaga tattttgaaa    1140
ccattaaacc tccagcattt atagattttc taggagttgg tcactaa                  1187
```

<210> SEQ ID NO 2
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Codon optimized for optimal expression in
    soybean (Glycine max); mol_type = unassigned DNA

<400> SEQUENCE: 2

```
atgaagatgg actttagctg cttcaagag taccccttcg agtttcactg taggggcact     60
acctttaacg gctttagaga gaacaacgcc gttagcgaga ctgtggaaga gttctgtaac    120
aagcgtagga tgcagaagaa gtcagacgac cttaagacta agaagaagaa gaaacagtca    180
gttagtaggg tgtgctctag gggccattgg aggattagtg aggatactca gctcatggaa    240
ctcgtttcag tttacggacc tcagaactgg aatcatattg ccgagtctat gcaaggtagg    300
accggtaaga gttgtaggct tcgttggttt aatcagctcg accctaggat taacaagagg    360
gcctttagtg acgaagagga agagaggctt cttgctgctc acagggcttt cggtaacaag    420
tgggctatga tcgctaagct cttaacggt aggaccgata acgcccttaa gaatcactgg    480
cacgtgctca tggctaggaa gatgaggcaa cagagttcta gctacgttca gaggtttaac    540
ggctcagctc acgagtctaa caccgatcac aagatcttta accttagccc aggccttagc    600
ctcctaaccc ttcatatctg tatcgagttt aactcagtga tcgtgatgag atacttaga    660 tacctttagcc ttaggaacaa cgagctgatg gtgtggtcac agaagtga                708
```

<210> SEQ ID NO 3
<211> LENGTH: 918
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<222> LOCATION: (1)..(918)
<223> OTHER INFORMATION: Codon optimized for optimal expression in
      soybean (Glycine max); mol_type = unassigned DNA

<400> SEQUENCE: 3

```
atgaagatgg actttagctg ctttcaagag tacccctccg agtttcactg tagggcact    60 acctttaacg gctttagaga gaacaacgcc gttagcgaga ctgtggaaga gttctgtaac   120
aagcgtagga tgcagaagaa gtcagacgac cttaagacta agaagaagaa gaaacagtca   180
gttagtaggg tgtgctctag gggccactgg cgtattagtg aggatactca gctaatggaa   240
ctagtttcag tctacggccc tcagaactgg aatcatatag ccgagtctat gcagggtagg   300
accggtaagt cttgtaggct tcgttggttt aatcagctag accctaggat taacaagcgc   360
gcctttagtg acgaagagga agagagacta ctagccgctc acagggcttt cggtaacaag   420
tgggctatga tagctaagct ctttaacggt aggaccgata cgcccttaa gaatcactgg    480 cacgtgctaa tggctaggaa gatgaggcag cagagttcta gctacgttca gcgctttaac   540
ggatcagctc acgagtctaa caccgatcac aagatcttta accttagccc cggtaacgtg   600
gacgacgacg aggacgttaa ccttaaaaag tgcagttggg agatgcttaa gagggcact    660 actaaccttta aggctcagta ccttcaagaa gagtactcta gctctaggat gcctatgcag   720
ggacctcacc accactactc taccttccca gctgatagcc tagctctaac ccttcacgtt   780
agtattcaag agcctagcag ttctagtagc cttagcctac ctagcagttc aactaccggt   840
gagcacacta tggtcactag atacttcgag actattaagc ccccagcctt tatagacttt   900
ctaggcgttg gtcactaa                                                 918
```

<210> SEQ ID NO 4
<211> LENGTH: 918
<212> TYPE: DNA
<213> ORGANISM: Arabidopsis thaliana
<220> FEATURE:
<221> NAME/KEY: misc_feature
<222> LOCATION: (1)..(918)
<223> OTHER INFORMATION: Nucleotide sequence of the second CDS (CDS2)
      sequence (At3g29020.2) of the MybTF gene; mol_type = unassigned
      DNA

<400> SEQUENCE: 4

```
atgaagatgg atttttcatg tttccaagaa tacccttttg agtttcattg cagaggaaca    60
acatttaatg ggtttagaga aaacaatgca gtgtctgaaa cagtagaaga gttctgtaat   120
aaaagaagga tgcagaagaa gagtgatgat ttgaagacta agaagaagaa gaaacagagt   180
gtttctaggg tttgtagtag aggacattgg aggatctctg aagatactca gcttatggag   240
cttgtttcgg tttacggtcc tcaaaactgg aaccacattg cagagagtat gcaaggaaga   300
acaggaaaga gctgcagatt gaggtggttt aaccagttag atccgaggat taacaagaga   360
gctttcagtg atgaagaaga agagagacta cttgctgctc atagagcttt tggtaacaaa   420
tgggctatga ttgctaagct ttttaatgga agaacagata tgccttgaa gaatcattgg    480 catgttctca tggcaaggaa gatgagacag caatcaagtt cttacgtcca agattcaat    540 ggttctgctc atgaatctaa cacagatcac aaaatcttca atctttctcc tggtaatgta   600
gatgatgatg aagatgtgaa tctgaaaaag tgcagctggg aaatgctaaa agagggaact   660
actaacctga aagctcagta tctccaagaa gaatatagtt cttcacgcat gccgatgcag   720
```

```
ggtccacatc atcactactc aaccttccct gcagattcct tggcactgac actgcatgtc    780
tccatccagg aaccatcatc atcatcgtca ttatcactgc catcatcatc aacaactgga    840
gaacatacaa tggtgaccag atattttgag accattaaac ctccagcatt tatagatttt    900
ctaggagttg gtcactaa                                                  918

<210> SEQ ID NO 5
<211> LENGTH: 305
<212> TYPE: PRT
<213> ORGANISM: Arabidopsis thaliana
<220> FEATURE:
<221> NAME/KEY: misc_feature
<223> OTHER INFORMATION: Amino acid sequence of the MybTF protein as
      derived from CDS2 nucleotide sequence

<400> SEQUENCE: 5
```

Met Lys Met Asp Phe Ser Cys Phe Gln Glu Tyr Pro Phe Glu Phe His
1               5                   10                  15

Cys Arg Gly Thr Thr Phe Asn Gly Phe Arg Glu Asn Asn Ala Val Ser
            20                  25                  30

Glu Thr Val Glu Glu Phe Cys Asn Lys Arg Arg Met Gln Lys Lys Ser
        35                  40                  45

Asp Asp Leu Lys Thr Lys Lys Lys Lys Gln Ser Val Ser Arg Val
    50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
                85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Thr Asp His Lys Ile
            180                 185                 190

Phe Asn Leu Ser Pro Gly Asn Val Asp Asp Asp Glu Asp Val Asn Leu
        195                 200                 205

Lys Lys Cys Ser Trp Glu Met Leu Lys Glu Gly Thr Thr Asn Leu Lys
    210                 215                 220

Ala Gln Tyr Leu Gln Glu Tyr Ser Ser Ser Arg Met Pro Met Gln
225                 230                 235                 240

Gly Pro His His His Tyr Ser Thr Phe Pro Ala Asp Ser Leu Ala Leu
                245                 250                 255

Thr Leu His Val Ser Ile Gln Glu Pro Ser Ser Ser Ser Leu Ser
            260                 265                 270

Leu Pro Ser Ser Ser Thr Thr Gly Glu His Thr Met Val Thr Arg Tyr
        275                 280                 285

Phe Glu Thr Ile Lys Pro Pro Ala Phe Ile Asp Phe Leu Gly Val Gly
    290                 295                 300

His
305

<210> SEQ ID NO 6
<211> LENGTH: 702
<212> TYPE: DNA
<213> ORGANISM: Arabidopsis thaliana
<220> FEATURE:
<221> NAME/KEY: source
<222> LOCATION: (1)..(702)
<223> OTHER INFORMATION: Nucleotide sequence of the first CDS (CDS1)
      sequence (At3g29020.1) of the MybTF gene; mol_type = unassigned
      DNA

<400> SEQUENCE: 6

```
atggattttt catgtttcca agaataccct tttgagtttc attgcagagg aacaacattt      60
aatgggttta gagaaaacaa tgcagtgtct gaaacagtag aagagttctg taataaaaga     120
aggatgcaga agaagagtga tgatttgaag actaagaaga agaagaaaca gagtgtttct     180
agggtttgta gtagaggaca ttggaggatc tctgaagata ctcagcttat ggagcttgtt     240
tcggtttacg gtcctcaaaa ctggaaccac attgcagaga gtatgcaagg aagaacagga     300
aagagctgca gattgaggtg gtttaaccag ttagatccga ggattaacaa gagagctttc     360
agtgatgaag aagaagagag actacttgct gctcatagac tttttggtaa caaatgggct     420
atgattgcta agcttttcaa tggaagaaca gataatgcct tgaagaatca ttggcatgtt     480
ctcatggcaa ggaagatgag acagcaatca agttcttacg tccaaagatt caatggttct     540
gctcatgaat ctaacacaga tcacaaaatc ttcaatcttt ctcctggttt gtctcttctt     600
accttacaca tatgcattga gtttaactct gttattgtaa tgagatactt tcgatattta     660
tcactcagga acaatgaact tatggtttgg tctcaaaagt ag                        702
```

<210> SEQ ID NO 7
<211> LENGTH: 233
<212> TYPE: PRT
<213> ORGANISM: Arabidopsis thaliana
<220> FEATURE:
<221> NAME/KEY: misc_feature
<223> OTHER INFORMATION: Amino acid sequence of the MybTF protein as
      derived from CDS1 nucleotide sequence

<400> SEQUENCE: 7

```
Met Asp Phe Ser Cys Phe Gln Glu Tyr Pro Phe Glu Phe His Cys Arg
1               5                  10                  15

Gly Thr Thr Phe Asn Gly Phe Arg Glu Asn Asn Ala Val Ser Glu Thr
            20                  25                  30

Val Glu Glu Phe Cys Asn Lys Arg Arg Met Gln Lys Lys Ser Asp Asp
        35                  40                  45

Leu Lys Thr Lys Lys Lys Lys Gln Ser Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
```

```
            145                 150                 155                 160
Leu Met Ala Arg Lys Met Arg Gln Gln Ser Ser Tyr Val Gln Arg
                165                 170                 175

Phe Asn Gly Ser Ala His Glu Ser Asn Thr Asp His Lys Ile Phe Asn
            180                 185                 190

Leu Ser Pro Gly Leu Ser Leu Leu Thr Leu His Ile Cys Ile Glu Phe
                195                 200                 205

Asn Ser Val Ile Val Met Arg Tyr Phe Arg Tyr Leu Ser Leu Arg Asn
    210                 215                 220

Asn Glu Leu Met Val Trp Ser Gln Lys
225                 230

<210> SEQ ID NO 8
<211> LENGTH: 1340
<212> TYPE: DNA
<213> ORGANISM: Arabidopsis thaliana
<220> FEATURE:
<221> NAME/KEY: misc_feature
<222> LOCATION: (1)..(1340)
<223> OTHER INFORMATION: Nucleotide sequence of the full-length genomic
      MybTF sequence (TAIR accession No 4010724011); mol_type =
      unassigned DNA

<400> SEQUENCE: 8
gtatatatga gacattagtt atagaagaga gactaacatg aagatggatt tttcatgttt      60
ccaagaatac cctttgagt tcattgcag aggaacaaca tttaatgggt ttagagaaaa       120
caatgcagtg tctgaaacag tagaagagtt ctgtaataaa agaaggatgc agaagaagag     180
tgatgatttg aagactaaga agaagaagaa acagagtgtt tctagggttt gtagtagagg     240
acattggagg atctctgaag atactcagct tatggagctt gtttcggttt acggtcctca     300
aaactggaac cacattgcag agagtatgca aggaagaaca ggtaacgaca aaaattgaaa     360
tctttaatct tcccttagct aattccggaa catgaaactt acaatgtttt ttcttgcttc     420
tttgtgtttt gtcttaaagg aaagagctgc agattgaggt ggtttaacca gttagatccg     480
aggattaaca agagagcttt cagtgatgaa gaagaagaga gactacttgc tgctcataga     540
gcttttggta acaaatgggc tatgattgct aagcttttca atggaagaac agataatgcc     600
ttgaagaatc attggcatgt tctcatggca aggaagatga gacagcaatc aagttcttac     660
gtccaaagat tcaatggttc tgctcatgaa tctaacacag atcacaaaat cttcaatctt     720
tctcctggtt tgtctcttct taccttacac atatgcattg agtttaactc tgttattgta     780
atgagatact ttcgatattt atcactcagg aacaatgaac ttatggtttg gtctcaaaag    840
tagtcagatt gcaagtttgg tgagtcttta agtttcatgg ttctgtgtgt tcttgcaggt     900
aatgtagatg atgatgaaga tgtgaatctg aaaaagtgca gctgggaaat gctaaaagag    960
ggaactacta acctgaaagc tcagtatctc caagaagaat atagttcttc acgcatgccg    1020
atgcagggtc cacatcatca ctactcaacc ttccctgcag attccttggc actgacactg    1080
catgtctcca tccaggaacc atcatcatca tcgtcattat cactgccatc atcatcaaca    1140
actggagaac atacaatggt gaccagatat tttgagacca ttaaacctcc agcatttata    1200
gattttctag gagttggtca ctaaagctct aacatttaga gtgggaacta atcaagaagt    1260
tgcttactcc tgtcattatt atcaaagtct ctgactttcc ttttgttagc cattaacatg    1320
acaagctaaa gacatcaagt                                                1340

<210> SEQ ID NO 9
```

```
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 1;
      mol_type = unassigned DNA

<400> SEQUENCE: 9
atgaaaatgg atttcagttg tttccaggaa tatccttttg aattccattg ccgagggacg      60
acattcaatg gattccggga aaataatgcg gtatcggaaa cggtggagga attttgcaat     120
aaaagacgaa tgcaaaaaaa atctgatgat ctaaaaacga aaaaaaaaaa gaagcaaagt     180
gtcagccgcg tttgttcccg gggacactgg cgcatatctg aagacacgca attgatggag     240
ctagtctctg tctatggacc acaaaattgg aaccacatcg cggaatccat gcagggacga     300
acagggaaat cctgccggct cagatggttc aaccaattgg atccacgtat caacaaacgt     360
gcgttctctg atgaggaaga ggaacgtctc ttagcagcgc atcgggcctt tgggaataaa     420
tgggcaatga ttgccaaatt attcaatggg cgtactgaca atgcgttgaa aaaccactgg     480
catgtgttga tggcgcgtaa aatgagacag caatcctcgt cttatgtcca acggttcaat     540
ggatccgcac atgaatcgaa tacgaccat aaaatattca atttatctcc tgggttgtcg      600
cttttgacgc tacacatttg catagaattc aattcggtta ttgtcatgag atatttcagg     660
tatctgtctt tacgcaataa tgaaatgatg gtatggtctc aaaaatag                  708

<210> SEQ ID NO 10
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 2;
      mol_type = unassigned DNA

<400> SEQUENCE: 10
atgaaaatgg atttctcctg tttccaggaa tatccttttg agttccattg caggggaacc      60
actttcaatg ggttccgaga aaataacgct gtctcagaaa cggtcgaaga attttgtaat     120
aaacgcagaa tgcaaaagaa atctgacgat ctcaaaacaa aaagaagaa aaaacaatcc     180
gtatcccgag tatgctccag agggcattgg cgaataagtg aagatactca gttgatggag     240
ttagtgagcg tatatggacc tcagaattgg aaccacatcg cggaatcaat gcaggggaga     300
acgggaaaaa gctgccggct acgctggttc aatcagttgg atcctcgtat taataaaagg     360
gccttcagcg atgaggaaga ggaacgactc ctggctgcgc atcgggcatt cggaaataag     420
tgggcaatga ttgccaagtt gttcaacggt cggacggaca atgcccttaa aaaccattgg     480
cacgttctaa tggcgaggaa aatgcggcag caaagttcca gttatgtcca acgtttcaat     540
ggctccgcgc atgaatccaa tacagaccat aaaatattca atctatctcc aggcctgtct     600
ctattaacac tacacatatg cattgaattc aactccgtca tagttatgcg ttattttagg     660
tatttgtctt tacgcaataa tgaaatgatg gtatggagcc agaaatga                  708

<210> SEQ ID NO 11
<211> LENGTH: 708
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 3;
      mol_type = unassigned DNA

<400> SEQUENCE: 11
atgaagatgg atttcagttg tttccaggag tatcccttrg aatttcattg tagagggact      60
acctttaacg ggttccgcga aaacaatgcc gttttccgaaa ccgtggagga gttttgtaat    120
aaacgtagaa tgcaaaaaaa aagcgacgat cttaagacca aaaaaaaaaa gaagcagtcc    180
gtgagccgcg tgtgttcaag gggccactgg cgtatcagtg aggacactca attaatggag    240
ctcgtatccg tatacggccc gcaaaattgg aatcatattg cagagtccat gcaggggaga    300
accggaaagt catgccgtct taggtggttc aaccaactag atcctcgaat aaataaacgg    360
gccttcagtg atgaggaaga ggaacggcta cttgctgccc acagggcttt tggaaataaa    420
tgggccatga ttgcaaagct cttcaatggc aggaccgaca atgcgttaaa aaaccattgg    480
catgtgctca tggctcggaa aatgagacaa caaagtagta gctatgttca gcgcttcaat    540
ggcagtgctc atgaatcaaa cacggaccac aaaattttca atttgtctcc tggcctctct    600
ttactaacct tacacatttg tatcgaattc aatagcgtga tcgtcatgcg gtacttccgc    660
taccttagcc tcaggaacaa cgagctgatg gtttggtcac aaaaatga              708

<210> SEQ ID NO 12
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 4;
      mol_type = unassigned DNA

<400> SEQUENCE: 12
atgaaaatgg atttctcatg cttttcaggag taccccttcg aattccactg cagaggcacc     60
acattcaatg ggttcagaga gaacaacgcc gtctcggaga ctgtagaaga gttctgtaat    120
aaacggcgca tgcagaaaaa atcagacgat cttaagacca aaagaagaa aaaacaatca    180 gttagtaggg tttgcagcag ggggcactgg cggattagtg aggatacgca gctgatggag    240
ctcgtctcgg tatatggtcc acaaaactgg aaccatattg cggagtctat gcaggggcgg    300
acaggcaaga gttgtaggct tcgttggttt aatcaactcg atcctcgcat aaacaagcgg    360 gcttttttcgg atgaagaaga ggagaggctt ctagctgctc accgggcctt cggtaataaa    420
tgggcgatga tcgcgaagct cttcaatggt cgtaccgaca tgccctgaa gaatcattgg    480 catgtgctca tggctcgtaa gatgaggcag cagagttcta gctacgtaca gcgcttcaat    540
gggtcggctc acgagtccaa caccgatcat aaaatcttta accttagccc cgggctgagc    600
ttattaacac tccatatttg tattgaattc aatagtgtga tcgtgatgag gtactttaga    660
tacctgagtt tacggaataa cgagatgatg gtgtggtcac agaagtga             708

<210> SEQ ID NO 13
<211> LENGTH: 708
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 5;
      mol_type = unassigned DNA

<400> SEQUENCE: 13
atgaagatgg actttagctg cttccaagaa taccccttcg aatttcactg cagggggtact    60 acgttcaacg gctttagaga aaacaacgca gttagcgaaa ctgtggagga gttctgcaac   120
aaacgtagga tgcagaagaa gtcagatgac ttgaaaacta aaagaaaaa gaagcaaagc    180 gttagtaggg tgtgttctag ggggcattgg aggatttccg aagatactca gctgatggag   240
ctcgttagcg tttacggccc tcagaactgg aaccacattg ccgagtctat gcagggtagg   300
accggaaagt cctgtaggct tcgttggttt aatcagctcg accctaggat taacaagcgg   360
gcttttagtg acgaggagga ggagaggctt ctagctgctc atcgggcttt cggtaacaag   420
tgggctatga tcgctaaatt attcaacggt cgtaccgata acgcccttaa gaaccattgg   480
cacgtgctca tggcacgcaa gatgaggcag cagagttcta gctatgttca gaggtttaac   540
ggctcagctc acgagtctaa cacagaccat aagattttta atctgtcacc aggccttagt   600
ctactaacct acatatatg tattgagttt aatagcgtga tagtgatgag atattttaga    660
taccttagcc taaggaacaa cgaactgatg gtctggtcac aaaagtga                708

<210> SEQ ID NO 14
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 6;
      mol_type = unassigned DNA

<400> SEQUENCE: 14
atgaagatgg acttttcctg cttttcaagag taccccttcg agtttcactg tagggggcact   60 acctttaacg gcttcagaga gaataacgca gttagcgaga ctgtagagga gttctgtaat   120
aagcgtcgta tgcagaagaa gtcagatgac ctcaagacta agaagaagaa aaaacaaagt   180
gtgagtaggg tgtgctctag gggccattgg aggatcagtg aggatacgca gctcatggag   240
cttgtttcag tttacggacc tcaaaactgg aaccatatcg ccgaatctat gcaaggtagg   300
accggtaaga gttgtaggct tcgttggttc aatcagctag accgcgaat caacaagagg   360 gcctttagtg acgaagagga agagaggctt ttagctgctc acagggcatt tggtaataag   420
tgggctatga tcgccaagtt gtttaacggt aggacggaca acgcgcttaa gaatcactgg   480
cacgtgctca tggcaaggaa gatgaggcaa caaagttctt catatgtcca gcgttttaat   540
ggcagtgctc acgaatctaa caccgatcac aagatcttca accttagccc cgggcttagc   600
ctcctaaccc tcacatctg tatcgagttc aacagcgtca tcgtgatgag atattttcgc    660
taccttagcc ttaggaataa cgagctgatg gtgtggtcac aaaaatga                708

<210> SEQ ID NO 15
<211> LENGTH: 708
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 7;
      mol_type = unassigned DNA

<400> SEQUENCE: 15
atgaagatgg attttagctg tttccaagag taccccttcg agtttcactg caggggcact      60
accttcaacg gctttagaga gaacaacgcc gttagcgaga ctgtggaaga gttctgtaac     120
aagcgtagga tgcagaaaaa gtcggacgac ctcaagacta aaaagaagaa gaaacagtca     180
gttagtaggg tgtgctcgag aggccattgg aggattagtg aggacacgca gctcatggaa     240
ctcgtttcag tgtacggacc tcagaattgg aaccatattg cagagtctat gcaaggtagg     300
actggtaaaa gttgcaggct tcgttggttt aaccagctcg atcctcgtat taacaagagg     360
gcctttagtg acgaagagga agagaggctt cttgctgctc acagggcttt cgggaataag     420
tgggctatga tcgctaagct cttttaacggt aggaccgata cgctcttaa gaaccactgg     480 cacgtactca tggctaggaa gatgaggcaa cagagttcta gctacgttca gaggtttaat     540
ggctcggctc acgaatctaa cacgatcac aagatcttta acttgagccc aggccttagc     600
ctcctaaccc tgcatatctg tatcgagttt aactcagtga tcgtgatgag atactttaga     660
taccttagcc ttaggaacaa cgaactgatg gtgtggtcgc agaagtga                 708

<210> SEQ ID NO 16
<211> LENGTH: 708
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(708)
<223> OTHER INFORMATION: Nucleotide sequence MybTF, variant 8;
      mol_type = unassigned DNA

<400> SEQUENCE: 16
atgaagatgg acttcagctg ctttcaagag taccccttcg agtttcactg tagggggcact     60 accttttaacg gcttcagaga gaacaacgcc gttagcgaaa ctgtggaaga gttctgtaac    120
aagcgtagga tgcagaagaa atcagacgac cttaagacta agaagaagaa gaagcagtca    180
gttagtaggg tgtgctctag gggccattgg aggattagtg aggatactca gctgatggaa    240
ctcgtttcag tgtacggacc tcagaactgg aatcacattg ccgagtctat gcaaggtagg    300
accggtaagt cgtgtaggct tcgttggttt aatcagctcg accctcggat taacaagagg    360
gcctttagtg acgaagagga agagaggctt ctagcagctc acagggcttt cggtaacaag    420
tgggctatga tcgctaagct cttttaatggt aggaccgata tgcccttaa aaatcactgg    480 catgtgctca tggctaggaa gatgaggcaa cagagttcta gctacgttca gcgctttaac    540
ggctcagctc acgagtctaa caccgatcac aagatcttta acctttctcc cggccttagc    600
ctcctaaccc ttcatatctg tatcgagttt aattcagtga ttgtgatgag atactttaga    660
tacctaagcc ttaggaacaa cgagctgatg gtgtggtcac agaagtga                 708

<210> SEQ ID NO 17
<211> LENGTH: 918
<212> TYPE: DNA
<213> ORGANISM: Artificial Sequence
<220> FEATURE:
```

<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 9;
      mol_type = unassigned DNA

<400> SEQUENCE: 17

```
atgaaaatgg atttctcctg tttccaggaa tatccatttg aattccattg cagagggacc      60
actttcaatg gcttcagaga aaataatgca gtatcagaaa ccgttgagga attttgcaat     120
aaacgaagaa tgcaaaaaaa atccgatgat ctgaaaacca aaaaaaaaaa aaagcaatca     180
gtgagccgcg tctgttctcg aggacattgg agaataagcg aagacacaca actcatggag     240
ctggtaagcg tatatggacc gcaaaattgg aaccatattg ctgaatccat gcaaggcaga     300
acaggcaaaa gttgccgtct gagatggttc aatcaattgg atccacgcat aaataaaagg     360
gcgttcagcg atgaggaaga ggaaaggctt ctcgctgccc acagagcgtt tggcaataaa     420
tgggcgatga ttgccaaatt gttcaatggc agaacggaca atgcattgaa aaaccattgg     480
catgtcttaa tggcccgtaa aatgaggcaa caatcctcat cttatgtcca acgtttcaat     540
ggcagcgcac atgaatccaa tacagaccat aaaatcttca atctatcgcc tggcaatgtt     600
gatgatgatg aagatgtaaa tctaaagaaa tgttcctggg aaatgctgaa ggaaggtaca     660
acgaatctaa aggcccaata tctccaggag gaatatagtt ccagtcgaat gccaatgcaa     720
ggcccgcatc atcattattc cacttttccc gcggatagtt tggctcttac attacatgta     780
tccatacagg aaccctcttc gagctcctcc ctgtcattac cgtcttcaag caccacaggg     840
gaacatacga tggttacgcg ttattttgaa acaataaaac cgcccgcgtt cattgatttc     900
ttaggtgtgg ggcattag                                                   918
```

<210> SEQ ID NO 18
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 10;
      mol_type = unassigned DNA

<400> SEQUENCE: 18

```
atgaaaatgg acttcagttg tttccaagaa tatcctttcg aattccattg caggggcacc      60
acgtttaatg gcttcagaga gaataatgcg gtaagtgaaa ccgtcgagga attttgcaat     120 aaagaagaa tgcaaaaaaa gagcgacgat ttaaaaacaa aaagaaaaa aaagcaaagc      180 gtcagtcgtg tctgtagtcg cggacattgg cgtatctccg aagatacgca actcatggag     240
ctcgtctccg tgtatggtcc gcaaaattgg aaccatattg ccgaaagcat gcaaggacgt     300
accgggaaat cttgcagatt gcggtggttc aaccagctcg atcctagaat aaataaacga     360
gccttctctg acgaggaaga ggaacgccta cttgcagcgc atagagcgtt cggaaataaa     420
tgggcgatga ttgcgaagct ttttaatggg aggaccgata acgccttaaa aaatcattgg     480
catgtcttaa tggcgaggaa aatgcgtcaa caatcatcta gctatgtcca acggtttaat     540
ggttcggcgc atgaatcgaa tacagaccat aaaatattca atttgtcccc tggcaacgta     600
gatgatgatg aggatgttaa tctcaagaaa tgcagttggg agatgctaaa ggaagggacg     660
accaatttaa aagctcaata tttgcaagag gagtatagta gctcacgcat gcccatgcaa     720
```

```
ggcccccacc accattattc gacgtttcca gcggatagtt tagcccttac attgcatgta    780
tccatacagg agcccagtag ctcctctagt ctttcgctgc cctcctcttc aaccacggga    840
gaacatacca tggttacgcg ttattttgaa acgatcaagc ccccggcttt cattgatttc    900
ctgggagtcg gtcattaa                                                  918
```

<210> SEQ ID NO 19
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 11;
      mol_type = unassigned DNA

<400> SEQUENCE: 19

```
atgaaaatgg atttcagctg tttccaggaa taccccttig aatttcactg taggggcact     60
acgtttaatg gcttcagaga aaataatgct gtttcggaga ccgtagaaga attttgcaat    120
aaacgccgga tgcaaaagaa aagtgatgac ttgaaaacga agaagaaaaa aaagcaatca    180
gtttcccgcg tgtgttcaag ggggcactgg cgaatcagtg aagacactca gctaatggag    240
ttagtttcag tctatggtcc gcaaaactgg aaccatatag ctgagtcgat gcaaggtcgt    300
acagggaagt catgtcgact tagatggttc aaccagttgg atcctcgcat caacaagcgt    360
gcgtttagtg atgaggagga ggaacgtcta ctagccgccc atcgagcgtt tggaaacaag    420
tgggctatga tcgcgaagtt attcaatgga cggactgaca acgcccttaa aaaccattgg    480
catgtattaa tggcaaggaa aatgcgtcaa cagtcttcta gctacgttca gagattcaac    540
ggatcagccc acgaatcaaa tacagaccat aaaattttta acctatcgcc tgggaatgta    600
gatgatgacg aagatgttaa cctcaaaaaa tgttcatggg agatgctaaa agaagggacg    660
acaaatttaa aagcccagta tttacaagaa gaatatagtt cctctcgtat gccaatgcaa    720
ggccctcacc accactacag tacatttcca gcagactcct tggctttgac tctacacgtg    780
tccatacagg aaccgtcctc ttcttcaagc cttagcctac ctagcagttc aaccaccggg    840
gaacatacca tggtgacaag atattttgaa accataaaac cacctgcatt catagatttc    900
ctaggcgtgg gtcactaa                                                  918
```

<210> SEQ ID NO 20
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 12;
      mol_type = unassigned DNA

<400> SEQUENCE: 20

```
atgaaaatgg actttagctg ctttcaagag tacccatttg aatttcactg tcggggcact     60
acgtttaacg gcttcagaga gaataacgcg gtttccgaga ctgtggagga ttctgcaac     120 aaacgtagga tgcaaaagaa gtcggacgac ctaaagacga aaagaagaa aaacaatca     180 gtcagtaggg tctgtagtcg aggccactgg aggattagtg aagacacaca gctaatggag    240
```

```
ctggtatcag tctacgggcc tcaaaattgg aaccacatag ccgagagtat gcaaggtagg      300
actggtaagt cttgtaggct taggtggttc aaccaacttg acccgcggat taacaagcgc      360
gccttcagcg atgaagagga agaaagactg ttggctgctc atagggcgtt cggcaacaag      420
tgggccatga tagctaagct cttcaatgga aggaccgaca acgccttaaa gaatcactgg      480
catgtgttaa tggcacgtaa gatgaggcaa caaagttctt cgtacgtgca gaggttcaac      540
ggtagtgcac acgagtcgaa caccgaccac aagatattca atcttagtcc cggaaatgtg      600
gatgatgacg aggatgttaa cctaaagaaa tgctcatggg aaatgcttaa ggagggtaca      660
actaatctta aggctcagta ccttcaggag gaatactcca gttctcgcat gcccatgcaa      720
ggtcctcacc atcactactc tacgtttcca gcagattcgt tagccttgac gctacatgtt      780
agtatacaag aaccttcatc ttctagtagt ctttctctcc ctagcagttc aacgacgggt      840
gagcatacga tggtcactcg gtatttcgag acgataaaac cgccagcctt catagacttc      900
ttaggggtag gtcactaa                                                   918

<210> SEQ ID NO 21
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 13;
      mol_type = unassigned DNA

<400> SEQUENCE: 21
atgaagatgg actttagctg ctttcaagag tatccattcg agtttcactg ccggggggacg       60 actttcaacg ggtttagaga aaataacgcc gttagcgaga ctgtagaaga gttctgtaat      120
aagcgtagga tgcagaagaa gtcggacgac ctgaaaacga aaagaagaa gaaacagtca      180 gtttcgcggg tgtgttcaag ggggcactgg cggatcagtg aggatactca gttaatggag      240
ttagtttcag tctacggccc tcagaactgg aatcatattg ccgagtcaat gcagggtcgc      300
accggcaagt cttgtaggct tcgctggttt aaccagttgg accctaggat taataagcgc      360
gccttcagtg acgaagagga agagagactc ttagccgcgc acagggcttt cggtaacaag      420
tgggcaatga ttgctaaact cttttaacggg aggactgata atgcccttaa gaatcattgg      480
catgtgctaa tggctagaaa gatgaggcaa cagagttcta gctatgtaca acggttcaac      540
ggttcagcgc acgagtccaa cacagatcat aaaatcttca acctttcgcc cggcaatgtg      600
gacgacgacg aggatgttaa cctgaagaag tgctcctggg agatgctgaa agagggcact      660
acgaacctta aggctcagta tctccaagaa gagtactcta gctctaggat gcctatgcaa      720
ggacctcacc accactattc taccttccca gccgatagcc tagctctaac cctacacgtc      780
tccattcaag agccttccag ttcttcaagc ctttccctac ctagcagtag cactaccggt      840
gaacacacta tggtcacgag atacttcgaa accattaagc caccagcctt tatagacttc      900
cttggcgtag gtcactga                                                   918

<210> SEQ ID NO 22
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(918)
<223> OTHER INFORMATION: Nucleotide sequence MybTF, variant 14;
      mol_type = unassigned DNA

<400> SEQUENCE: 22
atgaagatgg attttagctg ctttcaagag tacccctttg aattccactg tcgtggcact      60
acctttaacg ggtttagaga gaacaacgcc gtgtctgaga ctgtggaaga gttctgtaac     120
aagcgtagga tgcagaagaa gtcagatgac cttaaaacta agaaaaagaa gaagcagtca     180
gttagtcgtg tgtgcagtag gggccactgg agaattagtg aggatactca actaatggag     240
ctagtctcag tctacggccc tcaaaactgg aatcacatag ccgagtccat gcagggacgt     300
accggtaagt cttgcaggct tcgttggttc aatcaattgg accctaggat taataagcgc     360
gcctttagtg acgaagagga agagagactt ctagcagctc atcgagcttt cggtaataag     420
tgggctatga tagctaagct ctttaatggt cgcaccgaca atgcccttaa aaatcactgg     480
catgtcctaa tggctaggaa gatgcgtcag cagagctcta gctacgttca gcgcttcaac     540
ggaagcgcac atgagtctaa caccgatcat aagatcttta accttagccc cggtaacgtg     600
gacgacgatg aggatgttaa ccttaaaaag tgtagttggg agatgcttaa agagggcact     660
actaacctta aggctcaata tcttcaggag gaatattcta gctcgcggat gccgatgcag     720
ggaccgcacc accattactc taccttccca gctgattctc tagctctcac gctacacgtg     780
tcaattcaag agcctagcag ttctagtagc ttaagcctac cttcctcttc aactacaggt     840
gagcacacta tggtcactag atatttcgag actattaagc ccccgccttt atagactttt     900
tgggcgttgt tgtcactaa                                                  918

<210> SEQ ID NO 23
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 15;
      mol_type = unassigned DNA

<400> SEQUENCE: 23
atgaagatgg actttagctg ctttcaagag taccccttcg agtttcactg tagggggcact    60 acctttaacg gctttagaga gaacaatgcc gtttcagaga ctgtggagga gttctgtaac    120
aaacgtagga tgcaaaagaa gtccgacgac cttaaaacta agaagaagaa gaagcagtca    180
gttagtaggg tgtgctctag gggccattgg cgtatttctg aggataccca gctaatggaa    240
ctagtttcag tctacggccc gcagaactgg aatcatattg ccgaatctat gcagggtagg    300
accggtaagt cttgtcgtct tcgttggttt aaccagctag accctaggat aaacaagcgc    360
gccttcagtg acgaggagga agagagacta ctagccgccc atcgggcttt cggtaacaag    420
tgggcgatga tagctaagct ctttaacggt aggaccgata acgcccttaa gaatcactgg    480
catgtgctaa tggcaaggaa gatgaggcaa cagagttcta gctatgttca gcgctttaac    540
ggatcagctc acgagtctaa caccgatcac aagatcttta accttagccc cggtaatgtg    600
gacgacgacg aggacgtgaa ccttaaaaag tgcagttggg agatgcttaa agaaggcact    660
actaacctta aggctcaata cttacaagaa gagtattctt cgtctaggat gcctatgcag    720
ggacctcacc accactattc taccttccca gctgatagcc tagctctaac ccttcacgtt    780
```

```
agtattcaag agcctagctc ctcgagtagc ctgtccctac cttccagttc aactaccggt    840
gaacacacta tggtcactag atacttcgaa acgattaaac ccccagcctt tattgatttt    900
ctaggcgttg gtcactaa                                                  918
```

<210> SEQ ID NO 24
<211> LENGTH: 918
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(918)
<223> OTHER INFORMATION: Nucleotide sequence MybTF, variant 16;
      mol_type = unassigned DNA

<400> SEQUENCE: 24

```
atgaagatgg actttagctg ctttcaagag tacccatttg agttccactg tagggcact     60 accttcaacg gctttagaga gaacaacgcc gttagcgaga ctgtggaaga attctgtaat    120
aagcggagga tgcagaagaa gtcagacgac cttaagacca agaagaagaa gaaacagtca    180
gttagtaggg tgtgctctag gggtcactgg cgtataagtg aagatactca gctaatggaa    240
ctagtttcag tctacggccc tcagaactgg aatcatatag cagagtctat gcaaggtagg    300
accggtaagt cttgtaggct tcgttggttt aatcagctcg accctaggat taacaagcgc    360
gcctttagtg acgaagagga agagagacta ctagccgctc acagagcttt cggtaacaag    420
tgggctatga tagctaagct cttaaccggt aggaccgata acgcccttaa gaatcactgg    480
catgttctaa tggcgaggaa gatgaggcag cagagttcta gctacgttca gcgctttaac    540
ggatctgctc acgagtctaa cacagaccac aagatcttta accttagccc cggtaatgtg    600
gacgacgacg aggacgttaa tcttaaaaag tgcagttggg agatgcttaa agagggcact    660
actaacctta aggctcagta ccttcaagaa gagtactcta gctctaggat gcctatgcaa    720
ggaccgcacc accactactc tacgttccca gctgatagcc tagctctaac ccttcacgtt    780
agtattcaag agcctagcag ttctagtagc ctgagcctac ctagcagttc aactaccggt    840
gagcacacta tggtcactag atacttcgag actattaagc ccccagcctt tatagatttt    900
ctaggcgttg gtcactaa                                                  918
```

<210> SEQ ID NO 25
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 17;
      mol_type = unassigned DNA

<400> SEQUENCE: 25

```
atggactggt gcagcttcaa cgagtggccc ttcgagtacc acagcagaat cacctgctgg     60
aacatgtaca gagacaacca ggccctgacc gactgcgccg aggagttcag ccagagaaga    120
cacatgaaca gaaagaccga cgagatcaag acccacagaa gaagaaagca gagcgccagc    180
agagtgtgca gcagaggcca ctggagaatc agcgaggaca cccagctgat ggagctggtg    240
agcgtgtacg gcccccagaa ctggaaccac atcgccgaga gcatgcaggg cagaaccggc    300
```

```
aagagctgca gactgagatg gttcaaccag ctggacccca gaatcaacaa gagagccttc      360
agcgacgagg aggaggagag actgctggcc gcccacagag ccttcggcaa caagtgggcc      420
atgatcgcca agctgttcaa cggcagaacc gacaacgccc tgaagaacca ctggcacgtg      480
ctgatggcca gaaagatgag acagcagagc agcagctgga tcaacaagta ccagatcagc      540
gccaaggaca gcaacaccga gcacaagggc ttccagctga gccccatgat caccgccctg      600
tgcgtgaagc tgtgcgtgga cttccagagc gccgccgtgg ccagattctt caagttcctg      660
agcgtgagaa accaggagct gatcatgtac agcaacaga                              699
```

<210> SEQ ID NO 26
<211> LENGTH: 233
<212> TYPE: PRT
<213> ORGANISM: Artificial Sequence
<220> FEATURE:
<223> OTHER INFORMATION: Amino acid sequence MybTF, variant 17

<400> SEQUENCE: 26

```
Met Asp Trp Cys Ser Phe Asn Glu Trp Pro Phe Glu Tyr His Ser Arg
1               5                   10                  15

Ile Thr Cys Trp Asn Met Tyr Arg Asp Asn Gln Ala Leu Thr Asp Cys
            20                  25                  30

Ala Glu Glu Phe Ser Gln Arg Arg His Met Asn Arg Lys Thr Asp Glu
        35                  40                  45

Ile Lys Thr His Arg Arg Arg Lys Gln Ser Ala Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Trp Ile Asn Lys
                165                 170                 175

Tyr Gln Ile Ser Ala Lys Asp Ser Asn Thr Glu His Lys Gly Phe Gln
            180                 185                 190

Leu Ser Pro Met Ile Thr Ala Leu Cys Val Lys Leu Cys Val Asp Phe
        195                 200                 205

Gln Ser Ala Ala Val Ala Arg Phe Phe Lys Phe Leu Ser Val Arg Asn
    210                 215                 220

Gln Glu Leu Ile Met Tyr Ser Asn Arg
225                 230
```

<210> SEQ ID NO 27
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)

<223> OTHER INFORMATION: Nucleotide sequence MybTF, variant 18;
      mol_type = unassigned DNA

<400> SEQUENCE: 27

```
atggacttca gcacctggca ggagtggccc ttcgagtacc acagcaaggg caccagctgg      60
aacggctaca gagaccagaa catcatgtgc gacaccgtgg acgactactg caacaagaga     120
cacgcccaga agaagaccga ggaggccaga acccacaaga agaagcacca gagcgccagc     180
agagtgtgca gcagaggcca ctggagaatc agcgaggaca cccagctgat ggagctggtg     240
agcgtgtacg gcccccagaa ctggaaccac atcgccgaga gcatgcaggg cagaaccggc     300
aagagctgca gactgagatg gttcaaccag ctggacccca gaatcaacaa gagagccttc     360
agcgacgagg aggaggagag actgctggcc gcccacagag ccttcggcaa caagtgggcc     420
atgatcgcca agctgttcaa cggcagaacc gacaacgccc tgaagaacca ctggcacgtg     480
ctgatggcca gaaagatgag acagcagagc agctgctacg tgaacagatt caacctgagc     540
gccaaggaga gccagaccga cagacacatg tggaacgcca ccccctgct gtgcggcatc      600
agcctgaagg ccagcatcga ctacaactgc gtgatcatca tcagatggtt cagattcctg     660
agcctgcacc agaacgacct gatggtgtgg agcaacaga                            699
```

<210> SEQ ID NO 28
<211> LENGTH: 233
<212> TYPE: PRT
<213> ORGANISM: Artificial Sequence
<220> FEATURE:
<223> OTHER INFORMATION: Amino acid sequence MybTF, variant 18

<400> SEQUENCE: 28

```
Met Asp Phe Ser Thr Trp Gln Glu Trp Pro Phe Glu Tyr His Ser Lys
1               5                   10                  15

Gly Thr Ser Trp Asn Gly Tyr Arg Asp Gln Asn Ile Met Cys Asp Thr
            20                  25                  30

Val Asp Asp Tyr Cys Asn Lys Arg His Ala Gln Lys Lys Thr Glu Glu
        35                  40                  45

Ala Arg Thr His Lys Lys Lys His Gln Ser Ala Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Cys Tyr Val Asn Arg
                165                 170                 175

Phe Asn Leu Ser Ala Lys Glu Ser Gln Thr Asp Arg His Met Trp Asn
            180                 185                 190

Ala Thr Pro Leu Leu Cys Gly Ile Ser Leu Lys Ala Ser Ile Asp Tyr
        195                 200                 205

Asn Cys Val Ile Ile Ile Arg Trp Phe Arg Phe Leu Ser Leu His Gln
```

Asn Asp Leu Met Val Trp Ser Asn Arg
225                 230

<210> SEQ ID NO 29
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 19;
      mol_type = unassigned DNA

<400> SEQUENCE: 29
atggactaca ccacctggaa cgactggccc tgggactacc actgccacgg caccaccttc      60
aacatgttcc acgagaacaa cgccgtgacc gagtgcgtgg aggagttctg ccagcaccac     120
agaatgcaga agaagagcga ggagctgaag accagaagaa agcacaagaa cagcgtgagc     180
agagtgtgca gcagaggcca ctggagaatc agcgaggaca cccagctgat ggagctggtg     240
agcgtgtacg gcccccagaa ctggaaccac atcgccgaga gcatgcaggg cagaaccggc     300
aagagctgca gactgagatg gttcaaccag ctggacccca gaatcaacaa gagagccttc     360
agcgacgagg aggaggagag actgctggcc gcccacagag ccttcggcaa caagtgggcc     420
atgatcgcca agctgttcaa cggcagaacc gacaacgccc tgaagaacca ctggcacgtg     480
ctgatggcca gaaagatgag acagcagagc agcagctacg tgcagagatt caacggctgc     540
atgcacgaga ccaactgcga caagaaggcc tggaacctga gccccgtgct gaccctgctg     600
accggcaagg gcagcatcga cttccagagc gtgatcgcca tgagattctt caagtacctg     660
agcctgagaa accaggagct ggtgctgtac agccagaag                            699

<210> SEQ ID NO 30
<211> LENGTH: 233
<212> TYPE: PRT
<213> ORGANISM: Artificial Sequence
<220> FEATURE:
<223> OTHER INFORMATION: Amino acid sequence MybTF, variant 19

<400> SEQUENCE: 30

Met Asp Tyr Thr Thr Trp Asn Asp Trp Pro Trp Asp Tyr His Cys His
1               5                   10                  15

Gly Thr Thr Phe Asn Met Phe His Glu Asn Asn Ala Val Thr Glu Cys
            20                  25                  30

Val Glu Glu Phe Cys Gln His His Arg Met Gln Lys Lys Ser Glu Glu
        35                  40                  45

Leu Lys Thr Arg Arg Lys His Lys Asn Ser Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Glu Arg Leu
        115                 120                 125

Leu Ala Ala His Arg Ala Phe Gly Asn Lys Trp Ala Met Ile Ala Lys

```
                130                 135                 140
Leu Phe Asn Gly Arg Thr Asp Asn Ala Leu Lys Asn His Trp His Val
145                 150                 155                 160

Leu Met Ala Arg Lys Met Arg Gln Gln Ser Ser Tyr Val Gln Arg
                165                 170                 175

Phe Asn Gly Cys Met His Glu Thr Asn Cys Asp Lys Lys Ala Trp Asn
                180                 185                 190

Leu Ser Pro Val Leu Thr Leu Leu Thr Gly Lys Gly Ser Ile Asp Phe
                195                 200                 205

Gln Ser Val Ile Ala Met Arg Phe Phe Lys Tyr Leu Ser Leu Arg Asn
                210                 215                 220

Gln Glu Leu Val Leu Tyr Ser Gln Lys
225                 230

<210> SEQ ID NO 31
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 20;
      mol_type = unassigned DNA

<400> SEQUENCE: 31
atggactaca gcaccttcca ggactacccc ttcgagttca gtgcagagg caccaccttc      60 cagggctaca gagagcagaa cgccgtgagc gagagcgtgg aggagttctg caacaagaga    120
agaatgcagc acaagagcga ggacctgaga accaagcaca agagaaagaa cagcgtgagc    180
agagtgtgca gcagaggcca ctggagaatc agcgaggaca cccagctgat ggagctggtg    240
agcgtgtacg ccccccagaa ctggaaccac atcgccgaga gcatgcaggg cagaaccggc    300
aagagctgca gactgagatg gttcaaccag ctggacccca aatcaacaa gagagccttc    360 agcgacgagg aggaggagag actgctggcc gcccacagag ccttcggcaa caagtggggcc    420 atgatcgcca agctgttcaa cggcagaacc gacaacgccc tgaagaacca ctggcacgtg    480
ctgatggcca aaagatgag acagcagagc agctgctacg caacagatt caacatgacc    540 atccacgaga gcaacagcga cagaaagatc tacaacctga ccccggcct gtgcctgctg    600 agcctgcaca tcaccatcga gtggcagtgc gtgatcgtga tgagatactt cagatgggcc    660
accctgagaa caacgagct gctggtgttc agccagaag                            699

<210> SEQ ID NO 32
<211> LENGTH: 233
<212> TYPE: PRT
<213> ORGANISM: Artificial Sequence
<220> FEATURE:
<223> OTHER INFORMATION: Amino acid sequence MybTF, variant 20

<400> SEQUENCE: 32

Met Asp Tyr Ser Thr Phe Gln Asp Tyr Pro Phe Glu Phe Lys Cys Arg
1               5                   10                  15

Gly Thr Thr Phe Gln Gly Tyr Arg Glu Gln Asn Ala Val Ser Glu Ser
                20                  25                  30

Val Glu Glu Phe Cys Asn Lys Arg Arg Met Gln His Lys Ser Glu Asp
                35                  40                  45

Leu Arg Thr Lys His Arg Arg Lys Asn Ser Val Ser Arg Val Cys Ser
```

```
                50                  55                  60
Arg Gly His Trp Arg Ile Ser Glu Asp Thr Gln Leu Met Glu Leu Val
 65                  70                  75                  80

Ser Val Tyr Gly Pro Gln Asn Trp Asn His Ile Ala Glu Ser Met Gln
                 85                  90                  95

Gly Arg Thr Gly Lys Ser Cys Arg Leu Arg Trp Phe Asn Gln Leu Asp
                100                 105                 110

Pro Arg Ile Asn Lys Arg Ala Phe Ser Asp Glu Glu Glu Arg Leu
                115                 120                 125

Leu Ala Ala His Arg Ala Phe Gly Asn Lys Trp Ala Met Ile Ala Lys
                130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Cys Tyr Gly Asn Arg
                165                 170                 175

Phe Asn Met Thr Ile His Glu Ser Asn Ser Asp Arg Lys Ile Tyr Asn
                180                 185                 190

Leu Ser Pro Gly Leu Cys Leu Leu Ser Leu His Ile Thr Ile Glu Trp
                195                 200                 205

Gln Cys Val Ile Val Met Arg Tyr Phe Arg Trp Ala Thr Leu Arg Asn
210                 215                 220

Asn Glu Leu Leu Val Phe Ser Gln Lys
225                 230

<210> SEQ ID NO 33
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 21;
      mol_type = unassigned DNA

<400> SEQUENCE: 33
atggacttca gctgctggaa cgagtacccc ttcgagttca gatgcagaat caccagcttc     60
aacgcctgga gagagcagca ggccgtgagc gacaccgtgg aggagttctg caacaagaga    120
cacatgaaca agaagtgcga cgacctgaag accaagaaga agaagaagca gagcgtgagc    180
agagtgtgca gcagaggcca ctggagaatc agcgaggaca cccagctgat ggagctggtg    240
agcgtgtacg gcccccagaa ctggaaccac atcgccgaga gcatgcaggg cagaaccggc    300
aagagctgca gactgagatg gttcaaccag ctggacccca gaatcaacaa gagagccttc    360
agcgacgagg aggaggagag actgctggcc gcccacagag ccttcggcaa caagtgggcc    420
atgatcgcca agctgttcaa cggcagaacc gacaacgccc tgaagaacca ctggcacgtg    480
ctgatggcca gaaagatgag acagcagagc agcagctacg tgcagagatt caacgtgagc    540
ctgcacgaga gccagaccga gcacagaatc ttcaacggca gccccggcct gagcctgctg    600
tgcctgcaca tctgcatcga gttcaacacc gtgatcgtga tgagatactt ccactacctg    660
agcctgagaa acaacgagat catggtgtgg agccagaag                           699

<210> SEQ ID NO 34
<211> LENGTH: 233
<212> TYPE: PRT
<213> ORGANISM: Artificial Sequence
```

<220> FEATURE:
<223> OTHER INFORMATION: Amino acid sequence MybTF, variant 21

<400> SEQUENCE: 34

```
Met Asp Phe Ser Cys Trp Asn Glu Tyr Pro Phe Glu Phe Arg Cys Arg
1               5                   10                  15

Ile Thr Ser Phe Asn Ala Trp Arg Glu Gln Gln Ala Val Ser Asp Thr
            20                  25                  30

Val Glu Glu Phe Cys Asn Lys Arg His Met Asn Lys Lys Cys Asp Asp
        35                  40                  45

Leu Lys Thr Lys Lys Lys Lys Gln Ser Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Ser Tyr Val Gln Arg
                165                 170                 175

Phe Asn Val Ser Leu His Glu Ser Gln Thr Glu His Arg Ile Phe Asn
            180                 185                 190

Gly Ser Pro Gly Leu Ser Leu Leu Cys Leu His Ile Cys Ile Glu Phe
        195                 200                 205

Asn Thr Val Ile Val Met Arg Tyr Phe His Tyr Leu Ser Leu Arg Asn
    210                 215                 220

Asn Glu Ile Met Val Trp Ser Gln Lys
225                 230
```

<210> SEQ ID NO 35
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 22;
      mol_type = unassigned DNA

<400> SEQUENCE: 35

```
atggacttct gctgctacca ggagtggccc ttcgagttca gatgcagagg caccaccttc      60
aacggcttca gagagaacaa cctggtgagc gacaccggcg aggagttctg caacaagaga     120
agaatgcaga agagaagcga cgacctgaga agcaagaaga agaagaagca gagcgtgagc     180
agagtgtgca gcagagggcca ctggagaatc agcgaggaca cccagctgat ggagctggtg     240
agcgtgtacg gccccccagaa ctggaaccac atcgccgaga gcatgcaggg cagaaccggc     300
aagagctgca gactgagatg gttcaaccag ctggacccca gaatcaacaa gagagccttc     360
agcgacgagg aggaggagag actgctggcc gcccacagag ccttcggcaa caagtgggcc     420
```

| | |
|---|---:|
| atgatcgcca agctgttcaa cggcagaacc gacaacgccc tgaagaacca ctggcacgtg | 480 |
| ctgatggcca gaaagatgag acagcagagc agcagctacg tgcagagatt caacggcagc | 540 |
| gcccacgaga gcaacaccga ccacaagatc ttcaacgcca gccccggcct gagcggcctg | 600 |
| accctgcacc tgtgcatcga gttcaacagc gtgatcgtga tgagattcct gagatacctg | 660 |
| agcctgagac agcaggagat gatggtgtgg agccagaag | 699 |

<210> SEQ ID NO 36
<211> LENGTH: 233
<212> TYPE: PRT
<213> ORGANISM: Artificial Sequence
<220> FEATURE:
<223> OTHER INFORMATION: Amino acid sequence MybTF, variant 22

<400> SEQUENCE: 36

Met Asp Phe Cys Cys Tyr Gln Glu Trp Pro Phe Glu Phe Arg Cys Arg
1               5                   10                  15

Gly Thr Thr Phe Asn Gly Phe Arg Glu Asn Asn Leu Val Ser Asp Thr
            20                  25                  30

Gly Glu Glu Phe Cys Asn Lys Arg Arg Met Gln Lys Arg Ser Asp Asp
        35                  40                  45

Leu Arg Ser Lys Lys Lys Lys Gln Ser Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Ser Tyr Val Gln Arg
                165                 170                 175

Phe Asn Gly Ser Ala His Glu Ser Asn Thr Asp His Lys Ile Phe Asn
            180                 185                 190

Ala Ser Pro Gly Leu Ser Gly Leu Thr Leu His Leu Cys Ile Glu Phe
        195                 200                 205

Asn Ser Val Ile Val Met Arg Phe Trp Arg Tyr Leu Ser Leu Arg Gln
210                 215                 220

Gln Glu Met Met Val Trp Ser Gln Lys
225                 230

<210> SEQ ID NO 37
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 23;
      mol_type = unassigned DNA

<400> SEQUENCE: 37

```
atggacttca gctgcttcca ggagtacccc ttcgagttcc acaccaaggg caccaccttc      60
aacggcttca gagagaacaa cgccggcacc gagaccgtgg aggagttctg caacaagaga     120
agactgcaga agaagagcga cgacctgaag accaagaaga agaagaagca gagcgtgagc     180
agagtgtgca gcagaggcca ctggagaatc agcgaggaca cccagctgat ggagctggtg     240
agcgtgtacg gcccccagaa ctggaaccac atcgccgaga gcatgcaggg cagaaccggc     300
aagagctgca gactgagatg gttcaaccag ctggaccccca gaatcaacaa gagagccttc     360
agcgacgagg aggaggagag actgctggcc gcccacagag ccttcggcaa caagtgggcc     420
atgatcgcca agctgttcaa cggcagaacc gacaacgccc tgaagaacca ctggcacgtg     480
ctgatggcca gaaagatgag acagcagagc agcagctacg tgaacagatt ccagggcagc     540
gcccacgaga gcaacaccga ccacaagatc tggaacctga gccccggcct gagcctgctg     600
accctgcaca tctgcatcga gttcaactgc gtgatcgtga tgagatactt cagataccctg     660
tgcctgagaa acaacgacct gatggtgtgg agccagaag                            699
```

<210> SEQ ID NO 38
<211> LENGTH: 233
<212> TYPE: PRT
<213> ORGANISM: Artificial Sequence
<220> FEATURE:
<223> OTHER INFORMATION: Amino acid sequence MybTF, variant 23

<400> SEQUENCE: 38

```
Met Asp Phe Ser Cys Phe Gln Glu Tyr Pro Phe Glu Phe His Thr Lys
1               5                   10                  15

Gly Thr Thr Phe Asn Gly Phe Arg Glu Asn Asn Ala Gly Thr Glu Thr
            20                  25                  30

Val Glu Glu Phe Cys Asn Lys Arg Leu Gln Lys Lys Ser Asp Asp
        35                  40                  45

Leu Lys Thr Lys Lys Lys Lys Gln Ser Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160

Leu Met Ala Arg Lys Met Arg Gln Gln Ser Ser Ser Tyr Val Asn Arg
                165                 170                 175

Phe Gln Gly Ser Ala His Glu Ser Asn Thr Asp His Lys Ile Trp Asn
            180                 185                 190

Leu Ser Pro Gly Leu Ser Leu Leu Thr Leu His Ile Cys Ile Glu Phe
        195                 200                 205

Asn Cys Val Ile Val Met Arg Tyr Phe Arg Tyr Leu Cys Leu Arg Asn
    210                 215                 220

Asn Asp Leu Met Val Trp Ser Gln Lys
225                 230
```

<210> SEQ ID NO 39
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(699)
<223> OTHER INFORMATION: Nucleotide sequence MybTF, variant 24;
      mol_type = unassigned DNA

<400> SEQUENCE: 39

```
atggacttca gctgcttcca ggagtacccc ttcgagttcc actgcagagg caccaccttc      60
aacggcttca gagacaacaa cgccgtgagc gagagcgtgg aggagttctg caacaagaga     120
agaatgcaga agaagagcga cgacctgaag accaagaaga agcacaagca gaccgtgagc     180
agagtgtgca gcagaggcca ctggagaatc agcgaggaca cccagctgat ggagctggtg     240
agcgtgtacg gcccccagaa ctggaaccac atcgccgaga gcatgcaggg cagaaccggc     300
aagagctgca gactgagatg gttcaaccag ctggacccca gaatcaacaa gagagccttc     360
agcgacgagg aggaggagag actgctggcc gcccacagag ccttcggcaa caagtgggcc     420
atgatcgcca agctgttcaa cggcagaacc gacaacgccc tgaagaacca ctggcacgtg     480
ctgatggcca gaaagatgag acagcagagc agcagctacg tgcagagatt caacggcagc     540
gcccacgaga gcaacaccga ccacaagatc ttcaacctgt gccccggcct gagcctgctg     600
accctgcaca tctgcatcga gttcaacagc gtgatcgtga tgagatactg gagatacctg     660
agcctgagaa acaacgagct gatggtgtgg agccagaag                            699
```

<210> SEQ ID NO 40
<211> LENGTH: 233
<212> TYPE: PRT
<213> ORGANISM: Artificial Sequence
<220> FEATURE:
<223> OTHER INFORMATION: Amino acid sequence MybTF, variant 24

<400> SEQUENCE: 40

```
Met Asp Phe Ser Cys Phe Gln Glu Tyr Pro Phe Glu Phe His Cys Arg
1               5                   10                  15

Gly Thr Thr Phe Asn Gly Phe Arg Asp Asn Asn Ala Val Ser Glu Ser
            20                  25                  30

Val Glu Glu Phe Cys Asn Lys Arg Arg Met Gln Lys Lys Ser Asp Asp
        35                  40                  45

Leu Lys Thr Lys Lys Lys His Lys Gln Thr Val Ser Arg Val Cys Ser
    50                  55                  60

Arg Gly His Trp Arg Ile Ser Glu Asp Thr Gln Leu Met Glu Leu Val
65                  70                  75                  80

Ser Val Tyr Gly Pro Gln Asn Trp Asn His Ile Ala Glu Ser Met Gln
                85                  90                  95

Gly Arg Thr Gly Lys Ser Cys Arg Leu Arg Trp Phe Asn Gln Leu Asp
            100                 105                 110

Pro Arg Ile Asn Lys Arg Ala Phe Ser Asp Glu Glu Glu Glu Arg Leu
        115                 120                 125

Leu Ala Ala His Arg Ala Phe Gly Asn Lys Trp Ala Met Ile Ala Lys
    130                 135                 140

Leu Phe Asn Gly Arg Thr Asp Asn Ala Leu Lys Asn His Trp His Val
145                 150                 155                 160
```

Leu Met Ala Arg Lys Met Arg Gln Gln Ser Ser Tyr Val Gln Arg
                165                 170                 175

Phe Asn Gly Ser Ala His Glu Ser Asn Thr Asp His Lys Ile Phe Asn
        180                 185                 190

Leu Cys Pro Gly Leu Ser Leu Leu Thr Leu His Ile Cys Ile Glu Phe
    195                 200                 205

Asn Ser Val Ile Val Met Arg Tyr Trp Arg Tyr Leu Ser Leu Arg Asn
    210                 215                 220

Asn Glu Leu Met Val Trp Ser Gln Lys
225                 230

<210> SEQ ID NO 41
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 25;
      mol_type = unassigned DNA

<400> SEQUENCE: 41
atgagaggcg actggtgcag ctacaacgac ttcccctggg agttcaagac ccacatgagc     60
acctggaaca tgtggagaga gaacaacgcc gtgtgcgaga ccgtggagga ctactgccag    120
aagcaccaca tcaacaagaa gtgcgaggac atcaagaccc acaagaagca caagaacagc    180
gtgagcagag tgtgcagcag aggccactgg agaatcagcg aggacaccca gctgatggag    240
ctggtgagcg tgtacggccc ccagaactgg aaccacatcg ccgagagcat gcagggcaga    300
accggcaaga gctgcagact gagatggttc aaccagctgg accccagaat caacaagaga    360
gccttcagcg acgaggagga ggagagactg ctggccgccc acagagcctt cggcaacaag    420
tgggccatga tcgccaagct gttcaacggc agaaccgaca cgccctgaa gaaccactgg    480 cacgtgctga tggccagaaa gatgagacag cagagcagca gctacgtgca gagattcaac    540
ggcaccgcca gagagagcaa caccgagcac aagatcttca acctgagccc cgccaacgtg    600
gaggacgagg aggacggcca gatgcaccac accaccttcg acatcgtgag agacggcacc    660
agcaacctga aggccaacta cctgcaggag gagtacacct gcacccacgc ccccctgcag    720 ggcccccaaga agaagttcag cagctggccc gccgagtgcc tggtgatcac cgcccacatc    780
agcatcaacg accccagctg cagcagcagc atcagcctgc cctgctgctg caccaccggc    840
gagaagacca tgctgtgcag atacttcgac accatcaagc cccccatgtt cctggactgg    900
ctgggcctgg gcaga                                                    915

<210> SEQ ID NO 42
<211> LENGTH: 305
<212> TYPE: PRT
<213> ORGANISM: Artificial Sequence
<220> FEATURE:
<223> OTHER INFORMATION: Amino acid sequence MybTF, variant 25

<400> SEQUENCE: 42

Met Arg Gly Asp Trp Cys Ser Tyr Asn Asp Phe Pro Trp Glu Phe Lys
1               5                   10                  15

Thr His Met Ser Thr Trp Asn Met Trp Arg Glu Asn Asn Ala Val Cys
            20                  25                  30

Glu Thr Val Glu Asp Tyr Cys Gln Lys His His Ile Asn Lys Lys Cys
                35                  40                  45

Glu Asp Ile Lys Thr His Lys Lys His Lys Asn Ser Val Ser Arg Val
 50                  55                  60

Cys Ser Arg Gly His Trp Arg Ile Ser Glu Asp Thr Gln Leu Met Glu
 65                  70                  75                  80

Leu Val Ser Val Tyr Gly Pro Gln Asn Trp Asn His Ile Ala Glu Ser
                 85                  90                  95

Met Gln Gly Arg Thr Gly Lys Ser Cys Arg Leu Arg Trp Phe Asn Gln
                100                 105                 110

Leu Asp Pro Arg Ile Asn Lys Arg Ala Phe Ser Asp Glu Glu Glu Glu
            115                 120                 125

Arg Leu Leu Ala Ala His Arg Ala Phe Gly Asn Lys Trp Ala Met Ile
            130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Thr Ala Arg Glu Ser Asn Thr Glu His Lys Ile
            180                 185                 190

Phe Asn Leu Ser Pro Ala Asn Val Glu Asp Glu Glu Asp Gly Gln Met
            195                 200                 205

His His Thr Thr Phe Asp Ile Val Arg Asp Gly Thr Ser Asn Leu Lys
            210                 215                 220

Ala Asn Tyr Leu Gln Glu Glu Tyr Thr Cys Thr His Ala Pro Leu Gln
225                 230                 235                 240

Gly Pro Lys Lys Lys Phe Ser Ser Trp Pro Ala Glu Cys Leu Val Ile
                245                 250                 255

Thr Ala His Ile Ser Ile Asn Asp Pro Ser Cys Ser Ser Ser Ile Ser
                260                 265                 270

Leu Pro Cys Cys Cys Thr Thr Gly Glu Lys Thr Met Leu Cys Arg Tyr
            275                 280                 285

Phe Asp Thr Ile Lys Pro Pro Met Phe Leu Asp Trp Leu Gly Leu Gly
            290                 295                 300

Arg
305

<210> SEQ ID NO 43
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 26;
      mol_type = unassigned DNA

<400> SEQUENCE: 43
atgaagatgg acttctgcag ctacaacgag tggcccttcg agttcaagag ccacggcagc    60
acctacaacg cctggaagga caacaacgcc gtgtgcgact gcgtggagga cttctgcaac    120
aagcacaagc tgcagaagag aagcgacgac gccaagacca agaagaagca agaacagc     180 gtgagcagag tgtgcagcag aggccactgg agaatcagcg aggacaccca gctgatggag    240
ctggtgagcg tgtacggccc ccagaactgg aaccacatcg ccgagagcat gcagggcaga    300

```
accggcaaga gctgcagact gagatggttc aaccagctgg accccagaat caacaagaga    360
gccttcagcg acgaggagga ggagagactg ctggccgccc acagagcctt cggcaacaag    420
tgggccatga tcgccaagct gttcaacggc agaaccgaca acgccctgaa gaaccactgg    480
cacgtgctga tggccagaaa gatgagacag cagagcagca gctacgtgca gagattcaac    540
ggcaccctgc acgacaccaa caccgaccac cacgtgttcc agggcagccc cggcaacgtg    600
gaggacgacg acgacgtgaa cgtgagaaag tgctgctggg agatcatcaa ggagggcagc    660
acccagctga gagcccagtg ggcccaggac gagtacagca gcaccaaggg ccccatgcag    720
ggcccccaca gaaagtacag ctgcttcccc atcgagagca tggccctgag cctgcacgtg    780
accctgcagg accccagcag caccagcacc ggcaccctgc cagcacctg caccaccgtg    840 gagcacagca tggtgagcag atacttcgag accatcaagc ccccccctgtt catcgactac    900 gtgggcgtgg gccac                                                    915
```

<210> SEQ ID NO 44
<211> LENGTH: 305
<212> TYPE: PRT
<213> ORGANISM: Artificial Sequence
<220> FEATURE:
<223> OTHER INFORMATION: Amino acid sequence MybTF, variant 26

<400> SEQUENCE: 44

```
Met Lys Met Asp Phe Cys Ser Tyr Asn Glu Trp Pro Phe Glu Phe Lys
1               5                   10                  15

Ser His Gly Ser Thr Tyr Asn Ala Trp Lys Asp Asn Asn Ala Val Cys
            20                  25                  30

Asp Cys Val Glu Asp Phe Cys Asn Lys His Lys Leu Gln Lys Arg Ser
        35                  40                  45

Asp Asp Ala Lys Thr Lys Lys Lys His Lys Asn Ser Val Ser Arg Val
    50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
                85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Thr Leu His Asp Thr Asn Thr Asp His His Val
            180                 185                 190

Phe Gln Gly Ser Pro Gly Asn Val Glu Asp Asp Asp Val Asn Val
        195                 200                 205

Arg Lys Cys Cys Trp Glu Ile Ile Lys Glu Gly Ser Thr Gln Leu Arg
    210                 215                 220

Ala Gln Trp Ala Gln Asp Glu Tyr Ser Ser Thr Lys Gly Pro Met Gln
225                 230                 235                 240

Gly Pro His Arg Lys Tyr Ser Cys Phe Pro Ile Glu Ser Met Ala Leu
                245                 250                 255
```

Ser Leu His Val Thr Leu Gln Asp Pro Ser Ser Thr Ser Thr Gly Thr
        260                 265                 270

Leu Pro Ser Thr Cys Thr Thr Val Glu His Ser Met Val Ser Arg Tyr
        275                 280                 285

Phe Glu Thr Ile Lys Pro Pro Leu Phe Ile Asp Tyr Val Gly Val Gly
        290                 295                 300

His
305

<210> SEQ ID NO 45
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 27;
      mol_type = unassigned DNA

<400> SEQUENCE: 45
atgaagatgg actggagctg cttcaacgag ttcccttcg actacagaac cagactgtgc      60
accttcaacg ccttcagaga gcagaacgcc gtgagcgaga gcgtggagga ctggtgcaac    120
aagagaagaa tgcagcacca caccgaggac gtgagaacca agagaaagag aaagcagagc    180
gtgagcagag tgtgcagcag aggccactgg agaatcagcg aggacaccca gctgatggag    240
ctggtgagcg tgtacggccc ccagaactgg aaccacatcg ccgagagcat gcagggcaga    300
accggcaaga gctgcagact gagatggttc aaccagctgg accccagaat caacaagaga    360
gccttcagcg acgaggagga ggagagactg ctggccgccc acagagcctt cggcaacaag    420
tgggccatga tcgccaagct gttcaacggc agaaccgaca cgccctgaa gaaccactgg    480 cacgtgctga tggccagaaa gatgagacag cagagcagca gctacgtgca gagattcaac    540
ggcagcgccc acgagagcaa ctgcgagcac agagccttca acctgagccc cctgaacgtg    600
gaggaggacg acgacggcca gatgaagaag tgcagctggg agatgctgaa ggacggcacc    660
acccaggcca agctgcagtt cctgaacgag gactacagct gcagcagagt gcccgcccag    720
ggcccccaca gacactggag cacctt cccc gccgacagcg ccgccgtgac cctgaaggtg    780
agcatcaacg agcccagcac cagcaccagc ctgagcatcc cctgcagcag cagcaccgcc    840
gagcacacca tggtgaccag attcttcgag accatcaagc cccccgcctt catcgacttc    900
ctgggcgtgg gcaga                                                     915

<210> SEQ ID NO 46
<211> LENGTH: 305
<212> TYPE: PRT
<213> ORGANISM: Artificial Sequence
<220> FEATURE:
<223> OTHER INFORMATION: Amino acid sequence MybTF, variant 27

<400> SEQUENCE: 46

Met Lys Met Asp Trp Ser Cys Phe Asn Glu Phe Pro Phe Asp Tyr Arg
1               5                   10                  15

Thr Arg Leu Cys Thr Phe Asn Ala Phe Arg Glu Gln Asn Ala Val Ser
            20                  25                  30

Glu Ser Val Glu Asp Trp Cys Asn Lys Arg Arg Met Gln His His Thr
        35                  40                  45

Glu Asp Val Arg Thr Lys Arg Lys Arg Lys Gln Ser Val Ser Arg Val
 50                  55                  60

Cys Ser Arg Gly His Trp Arg Ile Ser Glu Asp Thr Gln Leu Met Glu
 65                  70                  75                  80

Leu Val Ser Val Tyr Gly Pro Gln Asn Trp Asn His Ile Ala Glu Ser
                 85                  90                  95

Met Gln Gly Arg Thr Gly Lys Ser Cys Arg Leu Arg Trp Phe Asn Gln
                100                 105                 110

Leu Asp Pro Arg Ile Asn Lys Arg Ala Phe Ser Asp Glu Glu Glu
                115                 120                 125

Arg Leu Leu Ala Ala His Arg Ala Phe Gly Asn Lys Trp Ala Met Ile
130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Tyr Val
                165                 170                 175

Gln Arg Phe Asn Gly Ser Ala His Glu Ser Asn Cys Glu His Arg Ala
                180                 185                 190

Phe Asn Leu Ser Pro Leu Asn Val Glu Glu Asp Asp Gly Gln Met
                195                 200                 205

Lys Lys Cys Ser Trp Glu Met Leu Lys Asp Gly Thr Thr Gln Ala Lys
210                 215                 220

Leu Gln Phe Leu Asn Glu Asp Tyr Ser Cys Ser Arg Val Pro Ala Gln
225                 230                 235                 240

Gly Pro His Arg His Trp Ser Thr Phe Pro Ala Asp Ser Ala Ala Val
                245                 250                 255

Thr Leu Lys Val Ser Ile Asn Glu Pro Ser Thr Ser Thr Ser Leu Ser
                260                 265                 270

Ile Pro Cys Ser Ser Ser Thr Ala Glu His Thr Met Val Thr Arg Phe
                275                 280                 285

Phe Glu Thr Ile Lys Pro Pro Ala Phe Ile Asp Phe Leu Gly Val Gly
                290                 295                 300

Arg
305

<210> SEQ ID NO 47
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 28;
      mol_type = unassigned DNA

<400> SEQUENCE: 47
atgcacatgg acttcagctg cttccaggag ttcccctacg agtggcactg cagagtgacc      60
accttcaacg gcttccacga caacaacgcc gtgagcgaga ccgtggagga gttctgcaac     120
aagagaagaa tgcagaagaa gagcgacgag ctgagaacca agaagaagaa gaagaacagc     180
gtgagcagag tgtgcagcag aggccactgg agaatcagcg aggacaccca gctgatggag     240
ctggtgagcg tgtacggccc ccagaactgg aaccacatcg ccgagagcat gcagggcaga     300
accggcaaga gctgcagact gagatggttc aaccagctgg accccagaat caacaagaga     360
gccttcagcg acgaggagga ggagagactg ctggccgccc acagagcctt cggcaacaag     420

```
tgggccatga tcgccaagct gttcaacggc agaaccgaca acgccctgaa gaaccactgg    480
cacgtgctga tggccagaaa gatgagacag cagagcagca gctacgtgca gagattcaac    540
ggcagcgccc acgagagcaa ctgcgacaga cacatcttca acctgacccc cggcaacgtg    600
gaggacgacg aggacgtgaa cctgaagcac tgcagcttcg acatcgtgaa ggagggcacc    660
tgcaacggca aggcccagta cggccaggag gactacagca gctgcagaat gcccatgaac    720 ggccccacc accactacag caccttcccc gccgacaccc tggccgccac cgcccacgtg    780
tgcatccagg agcccagcag ctgcagcacc gtgagcctgc ccagcagcag caccaccggc    840
gaccacaccg gcgtgaccca ctacttcgag agcatcagac cccccgcctt catcgactac    900
ctggccgtgg gcaga                                                     915
```

<210> SEQ ID NO 48
<211> LENGTH: 305
<212> TYPE: PRT
<213> ORGANISM: Artificial Sequence
<220> FEATURE:
<223> OTHER INFORMATION: Amino acid sequence MybTF, variant 28

<400> SEQUENCE: 48

```
Met His Met Asp Phe Ser Cys Phe Gln Glu Phe Pro Tyr Glu Trp His
1               5                   10                  15

Cys Arg Val Thr Thr Phe Asn Gly Phe His Asp Asn Asn Ala Val Ser
            20                  25                  30

Glu Thr Val Glu Glu Phe Cys Asn Lys Arg Arg Met Gln Lys Lys Ser
        35                  40                  45

Asp Glu Leu Arg Thr Lys Lys Lys Lys Asn Ser Val Ser Arg Val
    50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
                85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Cys Asp Arg His Ile
            180                 185                 190

Phe Asn Leu Thr Pro Gly Asn Val Glu Asp Asp Glu Asp Val Asn Leu
        195                 200                 205

Lys His Cys Ser Phe Asp Ile Val Lys Glu Gly Thr Cys Asn Gly Lys
    210                 215                 220

Ala Gln Tyr Gly Gln Glu Asp Tyr Ser Ser Cys Arg Met Pro Met Asn
225                 230                 235                 240

Gly Pro His His His Tyr Ser Thr Phe Pro Ala Asp Thr Leu Ala Ala
                245                 250                 255

Thr Ala His Val Cys Ile Gln Glu Pro Ser Ser Cys Ser Thr Val Ser
            260                 265                 270
```

```
Leu Pro Ser Ser Thr Thr Gly Asp His Thr Gly Val Thr His Tyr
        275                 280                 285

Phe Glu Ser Ile Arg Pro Pro Ala Phe Ile Asp Tyr Leu Ala Val Gly
        290                 295                 300

Arg
305

<210> SEQ ID NO 49
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 29;
      mol_type = unassigned DNA

<400> SEQUENCE: 49
atgaagatgg actacagctg cttccaggag taccccttcg acttccactg cagagccacc      60
accttcaacg gcttccacga gaacaacgcc gtgagcgaga ccgtggagga gttctgcaac     120
cacagaagaa tgcagaagaa gagcgacgac ggccacacca agagaaagaa gagacagagc     180
gtgagcagag tgtgcagcag aggccactgg agaatcagcg aggacaccca gctgatggag     240
ctggtgagcg tgtacggccc ccagaactgg aaccacatcg ccgagagcat gcagggcaga     300
accggcaaga gctgcagact gagatggttc aaccagctgg accccagaat caacaagaga     360
gccttcagcg acgaggagga ggagagactg ctggccgccc acagagcctt cggcaacaag     420
tgggccatga tcgccaagct gttcaacggc agaaccgaca cgccctgaa gaaccactgg     480 cacgtgctga tggccagaaa gatgagacag cagagcagca gctacgtgca gagattcaac     540
ggcagcgccc acgagagcaa cagcgaccac aaggtgttca acctgagccc cggcaacgtg     600
gacgaggacg aggacgtgaa cggcaagaag tgcagctacg agatgctgaa ggagggcagc     660
acccagctgc acgcccagta cctgcaggag gactacacca gcagcagaat gcccgcccag     720 ggccccacc accactacac cacctggccc gccgacagcc tggccctgac cctgcacgtg     780
tgcatccagg agcccagcag cagcagcagc atcagcatcc ccagcaccag caccaccggc     840
gagcacacca tgctgaccag atacttcgag accgtgaagc cccccgcctt catcgacttc     900
ctgggcgtgg gccac                                                     915

<210> SEQ ID NO 50
<211> LENGTH: 305
<212> TYPE: PRT
<213> ORGANISM: Artificial Sequence
<220> FEATURE:
<223> OTHER INFORMATION: Amino acid sequence MybTF, variant 29

<400> SEQUENCE: 50

Met Lys Met Asp Tyr Ser Cys Phe Gln Glu Tyr Pro Phe Asp Phe His
1               5                   10                  15

Cys Arg Ala Thr Thr Phe Asn Gly Phe His Glu Asn Asn Ala Val Ser
            20                  25                  30

Glu Thr Val Glu Glu Phe Cys Asn His Arg Arg Met Gln Lys Lys Ser
        35                  40                  45

Asp Asp Gly His Thr Lys Arg Lys Lys Arg Gln Ser Val Ser Arg Val
    50                  55                  60
```

Cys Ser Arg Gly His Trp Arg Ile Ser Glu Asp Thr Gln Leu Met Glu
 65                  70                  75                  80

Leu Val Ser Val Tyr Gly Pro Gln Asn Trp Asn His Ile Ala Glu Ser
                 85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Ser Asp His Lys Val
            180                 185                 190

Phe Asn Leu Ser Pro Gly Asn Val Asp Glu Asp Glu Asp Val Asn Gly
        195                 200                 205

Lys Lys Cys Ser Tyr Glu Met Leu Lys Glu Gly Ser Thr Gln Leu His
    210                 215                 220

Ala Gln Tyr Leu Gln Glu Asp Tyr Thr Ser Ser Arg Met Pro Ala Gln
225                 230                 235                 240

Gly Pro His His His Tyr Thr Thr Trp Pro Ala Asp Ser Leu Ala Leu
                245                 250                 255

Thr Leu His Val Cys Ile Gln Glu Pro Ser Ser Ser Ser Ile Ser
            260                 265                 270

Ile Pro Ser Thr Ser Thr Thr Gly Glu His Thr Met Leu Thr Arg Tyr
        275                 280                 285

Phe Glu Thr Val Lys Pro Pro Ala Phe Ile Asp Phe Leu Gly Val Gly
    290                 295                 300

His
305

<210> SEQ ID NO 51
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 30;
      mol_type = unassigned DNA

<400> SEQUENCE: 51
atgaagatgg acttcagctg cttccaggag tacccttcg agttccactg cagaggctgc      60
accttcaacg gcttcagaga gaacaacgcc gtgagcgaca ccgtggagga gttctgccag     120
aagagaaaga tgcagaagaa gtgcgacgac ctgagaacca gaagaagaa gaagcagagc     180 gtgagcagag tgtgcagcag aggccactgg agaatcagcg aggacacca gctgatggag     240 ctggtgagcg tgtacggccc ccagaactgg aaccacatcg ccgagagcat gcagggcaga     300
accggcaaga gctgcagact gagatggttc aaccagctgg accccagaat caacaagaga     360
gccttcagcg acgaggagga ggagagactg ctggccgccc acagagcctt cggcaacaag     420
tgggccatga tcgccaagct gttcaacggc agaaccgaca cgccctgaa gaaccactgg     480

```
cacgtgctga tggccagaaa gatgagacag cagagcagca gctacgtgca gagattcaac    540
ggcagcgccc acgagagcaa caccgaccac aagatcttcc agctgagccc cggcaacgtg    600
gacgacgacg aggacgtgca gctgaagaag tgcacctggg agatgctgag agacggcacc    660
accaacctga aggcccagta cctgaacgag gagtacacca gcagcagaat gcccatgaac    720
ggcccccacc accactacag caccttcccc gccgagagcc tggccatcac cctgcacgtg    780
agcgtgcagg agcccagcac cagcagctgc ctgagcctgc ccagcagcag ctgcaccgcc    840
gagcacaccc tggtgaccag atacttcgag accatcaagc ccccgccttt catcgacttc    900
ctgggcgtgg gcaga                                                    915
```

<210> SEQ ID NO 52
<211> LENGTH: 305
<212> TYPE: PRT
<213> ORGANISM: Artificial Sequence
<220> FEATURE:
<223> OTHER INFORMATION: Amino acid sequence MybTF, variant 30

<400> SEQUENCE: 52

```
Met Lys Met Asp Phe Ser Cys Phe Gln Glu Tyr Pro Phe Glu Phe His
 1               5                  10                  15

Cys Arg Gly Cys Thr Phe Asn Gly Phe Arg Glu Asn Asn Ala Val Ser
                20                  25                  30

Asp Thr Val Glu Glu Phe Cys Gln Lys Arg Lys Met Gln Lys Lys Cys
            35                  40                  45

Asp Asp Leu Arg Thr Lys Lys Lys Lys Gln Ser Val Ser Arg Val
        50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
                85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Thr Asp His Lys Ile
            180                 185                 190

Phe Gln Leu Ser Pro Gly Asn Val Asp Asp Glu Asp Val Gln Leu
        195                 200                 205

Lys Lys Cys Thr Trp Glu Met Leu Arg Asp Gly Thr Thr Asn Leu Lys
    210                 215                 220

Ala Gln Tyr Leu Asn Glu Glu Tyr Thr Ser Ser Arg Met Pro Met Asn
225                 230                 235                 240

Gly Pro His His His Tyr Ser Thr Phe Pro Ala Glu Ser Leu Ala Ile
                245                 250                 255

Thr Leu His Val Ser Val Gln Glu Pro Ser Thr Ser Ser Cys Leu Ser
            260                 265                 270

Leu Pro Ser Ser Ser Cys Thr Ala Glu His Thr Leu Val Thr Arg Tyr
        275                 280                 285
```

Phe Glu Thr Ile Lys Pro Pro Ala Phe Ile Asp Phe Leu Gly Val Gly
    290                 295                 300

Arg
305

<210> SEQ ID NO 53
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 31;
      mol_type = unassigned DNA

<400> SEQUENCE: 53
atgaagatgg agttcagctg cttccaggag ttccccttcg actggcactg caagggcacc      60
accttccagg gcttcagaga gcagaacgcc gtgagcgaga ccgtggagga gttctgcaac     120
aagagaagaa tgcagaagaa gagcgacgac ctgaagacca gagaaagaa gaagcagagc     180 gtgagcagag tgtgcagcag aggccactgg agaatcagcg aggacaccca gctgatggag     240
ctggtgagcg tgtacggccc ccagaactgg aaccacatcg ccgagagcat gcagggcaga     300
accggcaaga gctgcagact gagatggttc aaccagctgg accccagaat caacaagaga     360
gccttcagcg acgaggagga ggagagactg ctggccgccc acagagcctt cggcaacaag     420
tgggccatga tcgccaagct gttcaacggc agaaccgaca cgccctgaa gaaccactgg     480 cacgtgctga tggccagaaa gatgagacag cagagcagca gctacgtgca gagattcaac     540
ggcagcgccc acgagagcaa caccgacaga gaatcttca acctgagccc cggccaggtg     600
gacgacgacg aggacgtgaa cctgaagaag tgcagctggg agatgctgaa ggagggcacc     660
accaacctga aggcccagtt cctgcaggag gagtacagca gcagcagaat gcccatgcag     720
ggcccccacc accactacag caccttcccc gccgacagcc tggccctgag cctgagagtg     780
agcatccagg agcccagcag cagcagcagc ctgagcctgc cagcagctg caccaccggc     840 gagcacacca tggtgaccag atacttcgag agcatcaagc cccccgcctt catcgacttc     900
ctgggcgtgg gccac                                                     915

<210> SEQ ID NO 54
<211> LENGTH: 305
<212> TYPE: PRT
<213> ORGANISM: Artificial Sequence
<220> FEATURE:
<223> OTHER INFORMATION: Amino acid sequence MybTF, variant 31

<400> SEQUENCE: 54

Met Lys Met Glu Phe Ser Cys Phe Gln Glu Phe Pro Phe Asp Trp His
1               5                   10                  15

Cys Lys Gly Thr Thr Phe Gln Gly Phe Arg Glu Gln Asn Ala Val Ser
            20                  25                  30

Glu Thr Val Glu Glu Phe Cys Asn Lys Arg Arg Met Gln Lys Lys Ser
        35                  40                  45

Asp Asp Leu Lys Thr Lys Arg Lys Lys Gln Ser Val Ser Arg Val
    50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
            85                  90                  95

Met Gln Gly Arg Thr Gly Lys Ser Cys Arg Leu Arg Trp Phe Asn Gln
        100                 105                 110

Leu Asp Pro Arg Ile Asn Lys Arg Ala Phe Ser Asp Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Thr Asp Arg Arg Ile
            180                 185                 190

Phe Asn Leu Ser Pro Gly Gln Val Asp Asp Asp Glu Asp Val Asn Leu
        195                 200                 205

Lys Lys Cys Ser Trp Glu Met Leu Lys Glu Gly Thr Thr Asn Leu Lys
    210                 215                 220

Ala Gln Phe Leu Gln Glu Glu Tyr Ser Ser Ser Arg Met Pro Met Gln
225                 230                 235                 240

Gly Pro His His His Tyr Ser Thr Phe Pro Ala Asp Ser Leu Ala Leu
                245                 250                 255

Ser Leu Arg Val Ser Ile Gln Glu Pro Ser Ser Ser Ser Leu Ser
            260                 265                 270

Leu Pro Ser Ser Cys Thr Thr Gly Glu His Thr Met Val Thr Arg Tyr
        275                 280                 285

Phe Glu Ser Ile Lys Pro Pro Ala Phe Ile Asp Phe Leu Gly Val Gly
    290                 295                 300

His
305

<210> SEQ ID NO 55
<211> LENGTH: 915
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(915)
<223> OTHER INFORMATION: Nucleotide sequence MybTF, variant 32;
      mol_type = unassigned DNA

<400> SEQUENCE: 55
atgaagatgg acttcagctg cttccaggag tacccccttcg agttccactg cagaggcacc      60
accttcaacg gctggagaga gaacaacgcc gtgagcgaga ccgtggagga gttcacccag     120
agaagaagaa tgcagaagaa gaccgacgac ctgaagacca agaagaagaa gaagcagagc     180
gtgagcagag tgtgcagcag aggccactgg agaatcagcg aggacaccca gctgatggag     240
ctggtgagcg tgtacggccc ccagaactgg aaccacatcg ccgagagcat gcagggcaga     300
accggcaaga gctgcagact gagatggttc aaccagctgg accccagaat caacaagaga     360
gccttcagcg acgaggagga ggagagactg ctggccgccc acagagcctt cggcaacaag     420
tgggccatga tcgccaagct gttcaacggc agaaccgaca acgccctgaa gaaccactgg     480
cacgtgctga tggccagaaa gatgagacag cagagcagca gctacgtgca gagattcaac     540
ggcagcgccc acgagagcaa caccgaccac aagatcttca acctgacccc cggcaacgtg     600

-continued

```
gacgacgacg aggacgtgaa cctgaagaag tgcagctggg agatgctgaa ggagggcacc      660
accaacctga aggcccagta cctgcaggac gagtacagca gcagcagaat gcccatgcag      720 ggccccccacc accactacag caccttcccc gccgacagcc tggccctgac cctgcacgtg     780
agcatccagg agcccagcag caccagcagc ctgagcctgc caccagcag caccaccggc      840 gagcacacca tggtgaccag atacttcgag accatcaagc cccccgcctt catcgacttc      900
ctgggcgtgg gccac                                                       915
```

<210> SEQ ID NO 56
<211> LENGTH: 305
<212> TYPE: PRT
<213> ORGANISM: Artificial Sequence
<220> FEATURE:
<223> OTHER INFORMATION: Amino acid sequence MybTF, variant 32

<400> SEQUENCE: 56

```
Met Lys Met Asp Phe Ser Cys Phe Gln Glu Tyr Pro Phe Glu Phe His
1               5                   10                  15

Cys Arg Gly Thr Thr Phe Asn Gly Trp Arg Glu Asn Asn Ala Val Ser
            20                  25                  30

Glu Thr Val Glu Glu Phe Thr Gln Arg Arg Arg Met Gln Lys Lys Thr
        35                  40                  45

Asp Asp Leu Lys Thr Lys Lys Lys Lys Gln Ser Val Ser Arg Val
    50                  55                  60

Cys Ser Arg Gly His Trp Arg Ile Ser Glu Asp Thr Gln Leu Met Glu
65                  70                  75                  80

Leu Val Ser Val Tyr Gly Pro Gln Asn Trp Asn His Ile Ala Glu Ser
                85                  90                  95

Met Gln Gly Arg Thr Gly Lys Ser Cys Arg Leu Arg Trp Phe Asn Gln
            100                 105                 110

Leu Asp Pro Arg Ile Asn Lys Arg Ala Phe Ser Asp Glu Glu Glu Glu
        115                 120                 125

Arg Leu Leu Ala Ala His Arg Ala Phe Gly Asn Lys Trp Ala Met Ile
    130                 135                 140

Ala Lys Leu Phe Asn Gly Arg Thr Asp Asn Ala Leu Lys Asn His Trp
145                 150                 155                 160

His Val Leu Met Ala Arg Lys Met Arg Gln Gln Ser Ser Ser Tyr Val
                165                 170                 175

Gln Arg Phe Asn Gly Ser Ala His Glu Ser Asn Thr Asp His Lys Ile
            180                 185                 190

Phe Asn Leu Thr Pro Gly Asn Val Asp Asp Glu Asp Val Asn Leu
        195                 200                 205

Lys Lys Cys Ser Trp Glu Met Leu Lys Glu Gly Thr Thr Asn Leu Lys
    210                 215                 220

Ala Gln Tyr Leu Gln Asp Glu Tyr Ser Ser Ser Arg Met Pro Met Gln
225                 230                 235                 240

Gly Pro His His His Tyr Ser Thr Phe Pro Ala Asp Ser Leu Ala Leu
                245                 250                 255

Thr Leu His Val Ser Ile Gln Glu Pro Ser Ser Thr Ser Ser Leu Ser
            260                 265                 270
```

```
Leu Pro Thr Ser Ser Thr Thr Gly Glu His Thr Met Val Thr Arg Tyr
        275                 280                 285

Phe Glu Thr Ile Lys Pro Pro Ala Phe Ile Asp Phe Leu Gly Val Gly
        290                 295                 300

His
305
```

FUNGAL RESISTANT PLANTS EXPRESSING MYBTF

This application is a National Stage application of International Application No. PCT/EP2014/054461, filed Mar. 7, 2014, which claims priority under 35 U.S.C. § 119 to European Patent Application No. 13158321.3 filed Mar. 8, 2013, the entire content of which is hereby incorporated herein by reference.

REFERENCE TO SEQUENCE LISTING SUBMITTED VIA EFS-WEB

This application was filed electronically via EFS-Web and includes an electronically submitted sequences listing in .txt format. The .txt file contains a sequence listing entitled "74753-371_Seqlisting.txt" created on Aug. 31, 2015, and is 94,056 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the order Pucciniales, for example soybean rust, in plants, plant parts, and/or plant cells. This is achieved by increasing the expression and/or activity of a Myb-like transcription factor (MybTF) protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding a MybTF protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are in most cases directed against necrotrophic pathogens (and insects).

Another more specific resistance mechanism is based on the presence of so called resistance genes (R-genes). Most R genes belong to the nucleotide-binding site—leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that fungal pathogens, in particular of the order Pucciniales, for example soybean rust, can be controlled by increasing the expression of a MybTF protein. The MybTF described in this invention belongs to the R2R3-MYB family.

The present invention therefore provides a method of increasing resistance against fungal pathogens, preferably against rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more MybTF nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous MybTF nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust.

Surprisingly, we found that resistance against fungal pathogens, in particular of the order Pucciniales, for example soybean rust, can be enhanced by increasing the expression of a MybTF protein.

The present invention therefore provides a method of increasing resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust, in transgenic plants, transgenic plant parts, or transgenic plant cells by overexpressing one or more MybTF nucleic acids.

A further object is to provide transgenic plants resistant against fungal pathogens, preferably rust pathogens (i.e., fungal pathogens of the order Pucciniales), preferably of the family Phacopsoraceae, more preferably against fungal pathogens of the genus *Phacopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous MybTF nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

FIG. 2 shows the schematic illustration of the plant transformation vector harboring the fragment of MybTF DNA under control of the parsley ubiquitine promoter.

Figure 3:
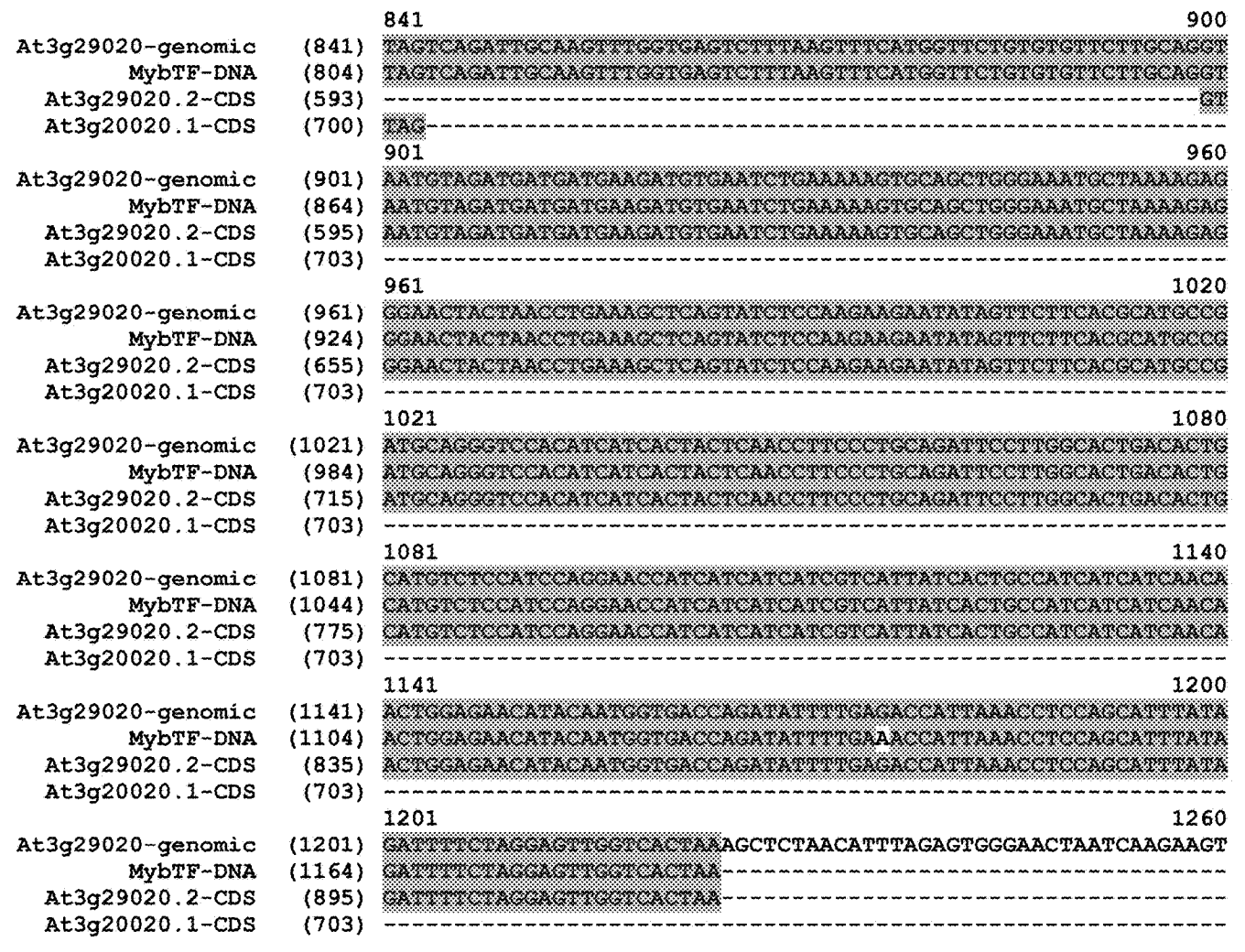

FIG. 3 shows the alignment of the *Arabidopsis* MybTF genomic sequence (AT3G29020-genomic, TAIR accession No 4010724011, SEQ ID NO: 8), the two putative coding sequences of MybTF, which are derived from the genomic sequence, MybTF CDS1 (At3G29020.1-CDS, accession No NM_113823, SEQ-ID NO: 6) and MybTF CDS2 (At3G29020.2-CDS, TAIR accession No 4010715313, SEQ ID NO: 4) and the sequence of the MybTF sequence as used in the examples (MybTF-DNA, SEQ ID NO: 1).

FIG. 4 shows the result of the scoring of 15 transgenic soy plants (To generation) expressing the MybTF overexpression vector construct. To soybean plants harbouring the MybTF expression cassette were inoculated with spores of *Phakopsora pachyrhizi*. The expression of the MybTF was checked by RT-PCR. The evaluation of the diseased leaf area on all leaves was performed 14 days after inoculation. The average of the percentage of the leaf area showing fungal colonies or strong yellowing/browning on all leaves was considered as diseased leaf area. At all 15 soybean To plants expressing the MybTF (expression checked by RT-PCR) were evaluated in parallel to non-transgenic control plants. The average of the diseased leaf area is shown in FIG. 4. Overexpression of MybTF significantly (***: $p<0.001$) reduces the diseased leaf area in comparison to non-transgenic control plants by 72.3%.

FIG. 5 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar functional activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over the entire length of the respective MybTF nucleic acid sequence or MybTF amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the SmithWaterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

Sequence identity between the nucleic acid or protein useful according to the present invention and the MybTF nucleic acids or MybTF proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the SmithWaterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986) The classification of amino acid conservation J Theor Biol., 119:205-18 and Table 1 below).

TABLE 1

Examples of conserved amino acid substitutions

| Residue | Conservative Substitutions | Residue | Conservative Substitutions |
|---|---|---|---|
| A | G, V, I, L, M | L | M, I, V, A, G |
| C | S, T | N | Q |
| E | D | Q | N |
| D | E | P | |
| G | A, V, I, L, M | S | T, C |
| F | Y, W | R | K, H |
| I | V, A, G, L, M | T | S, C |
| H | R, K | W | Y, F |
| K | R, H | V | I, A, G, L, M |
| M | L, I, V, A, G | Y | F, W |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in sflico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous MybTF nucleic acid, functional fragments thereof and/or an exogenous nucleic acid capable of hybridizing with a MybTF nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole MybTF nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous MybTF nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous MybTF nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more MybTF nucleic acids, all those constructions brought about by man by genetechnological methods in which either (a) the sequences of the MybTF nucleic acids or a part thereof, or
(b) genetic control sequence(s) which is operably linked with the MybTF nucleic acid sequence according to the invention, for example a promoter, or
(c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous MybTF nucleic acid, recombinant construct, vector or expression cassette including one or more MybTF nucleic acids is integrated into the genome by means of genetechnology.

A "wild type" plant, "wild type" plant part, or "wild type" plant cell means that said plant, plant part, or plant cell does not express exogenous MybTF nucleic acid or exogenous MybTF protein.

Natural locus means the location on a specific chromosome, preferably the location between certain genes, more preferably the same sequence background as in the original plant which is transformed.

Preferably, the transgenic plant, plant cell or tissue thereof expresses the MybTF nucleic acids, MybTF constructs or MybTF expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the MybTF nucleic acids has an identity as defined above over a length of at least 70%, at least 75%, at least 90% of the nucleotides of the respective MybTF nucleic acid.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective introncontaining genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the MybTF nucleotide sequence as defined by SEQ ID NO: 6, 4, 2, 3, or 1.

The term "increased activity" or "enhanced activity" as used herein means any protein having increased activity and which provides an increased fungal resistance compared with the wildtype plant merely expressing the respective endogenous MybTF nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

MybTF Nucleic Acids

The MybTF nucleic acid to be overexpressed in order to achieve increased resistance to fungal pathogens, e.g., of the family Phacopsoraceae, for example soybean rust, is preferably a nucleic acid coding for a MybTF protein, preferably of the R2R3-MYB family, and is preferably as defined by SEQ ID NO: 2, 3, 1, 6, 4, 8, 9-24, 25, 27, 29, 31, 33, 35, 37, 39, 41, 43, 45, 47, 49, 51, 53, or 55, or a fragment, homolog, derivative, orthologue or paralogue thereof, or a splice variant thereof. Preferably, the nucleic acid coding for a MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or is a functional fragment thereof, or a splice variant thereof. Most preferred is at least 90% identity, at least 92%, at least 95%, at least 97%, more preferred is at least 98% or at least 99% identity with SEQ ID NO: 2, 3, 1, 6, 4, 8, 9-24, 25, 27, 29, 31, 33, 35, 37, 39, 41, 43, 45, 47, 49, 51, 53, or 55.

Preferably, the MybTF nucleic acid to be overexpressed in order to achieve increased resistance to fungal pathogens, e.g., of the family Phacopsoraceae, for example soybean rust, is preferably a nucleic acid coding for a MybTF protein, and is preferably as defined by SEQ ID NO: 2, or a fragment, homolog, derivative, orthologue or paralogue thereof, or a splice variant thereof. Preferably, the nucleic acid coding for a MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 2 or is a functional fragment thereof, or a splice variant thereof. Most preferred is at least 90% identity, at least 92%, at least 95%, at least 97% identity, more preferred is at least 98% or at least 99% identity with SEQ ID NO: 2.

More preferably, the MybTF nucleic acid to be overexpressed in order to achieve increased resistance to fungal pathogens, e.g., of the family Phacopsoraceae, for example soybean rust, is preferably a nucleic acid coding for a MybTF protein, and is preferably as defined by SEQ ID NO: 1, or a fragment, homolog, derivative, orthologue or paralogue thereof, or a splice variant thereof. Preferably, the nucleic acid coding for a MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 1 or is a functional fragment thereof, or a splice variant thereof. Most preferred is at least 92%, at least 95%, at least 97% identity, more preferred is at least 98% or at least 99% identity with SEQ ID NO: 1.

Preferably, the MybTF nucleic acid to be overexpressed in order to achieve increased resistance to fungal pathogens, e.g., of the family Phacopsoraceae, for example soybean rust, is preferably a nucleic acid coding for a MybTF protein, and is preferably as defined by SEQ ID NO: 3, or a fragment, homolog, derivative, orthologue or paralogue thereof, or a splice variant thereof. Preferably, the nucleic acid coding for a MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 3 or is a functional fragment thereof, or a splice variant thereof. Most preferred is at least 90% identity, at least 92%, at least 95%, at least 97% identity, more preferred is at least 98% or at least 99% identity with SEQ ID NO: 3.

Preferably the MybTF nucleic acid is an isolated nucleic acid molecule consisting of or comprising a nucleic acid selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 3, 1, 6, 4, 8, 9-24, 25, 27, 29, 31, 33, 35, 37, 39, 41, 43, 45, 47, 49, 51, 53, or 55, or a functional fragment, derivative, orthologue, or paralogue thereof, or a splice variant thereof;

(ii) a nucleic acid encoding a MybTF protein comprising an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, 5, 26, 28, 30, 32, 34, 36, 38, 40, 42, 44, 46, 48, 50, 52, 54, or 56, or a functional fragment, derivative, orthologue, or paralogue thereof; preferably the MybTF protein has essentially the same biological activity as a MybTF protein encoded by SEQ ID NO: 2, 3, 1, 6, or 4; preferably the MybTF protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 5 or 7; preferably the encoded protein confers enhanced fungal resistance relative to control plants; and (iv) a nucleic acid encoding the same MybTF protein as the MybTF nucleic acids of (i) to (iii) above, but differing from the MybTF nucleic acids of (i) to (iii) above due to the degeneracy of the genetic code.

Preferably the MybTF nucleic acid is an isolated nucleic acid molecule consisting of or comprising a nucleic acid selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 8, or a functional fragment, derivative, orthologue, or paralogue thereof, or a splice variant thereof;

(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7 or 5, or a functional fragment, derivative, orthologue, or paralogue thereof; preferably the MybTF protein has essentially the same biological activity as a MybTF protein encoded by SEQ ID NO: 1 or 8, preferably the MybTF protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and (iv) a nucleic acid encoding the same MybTF protein as the MybTF nucleic acids of (i) to (iii) above, but differing from the MybTF nucleic acids of (i) to (iii) above due to the degeneracy of the genetic code.

Preferably the MybTF nucleic acid is an isolated nucleic acid molecule comprising a nucleic acid selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2 or 3, or a functional fragment, derivative, orthologue, or paralogue thereof, or a splice variant thereof;

(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7 or 5, or a functional fragment, derivative, orthologue, or paralogue thereof; preferably the MybTF protein has essentially the same biological activity as a MybTF protein encoded by SEQ ID NO: 2 or 3, preferably the MybTF protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and (iv) a nucleic acid encoding the same MybTF protein as the MybTF nucleic acids of (i) to (iii) above, but differing from the MybTF nucleic acids of (i) to (iii) above due to the degeneracy of the genetic code.

Preferably the MybTF nucleic acid is an isolated nucleic acid molecule comprising a nucleic acid selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2 or 6, or a functional fragment, derivative, orthologue, or paralogue thereof, or a splice variant thereof;

(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, or a functional fragment, derivative, orthologue, or paralogue thereof; preferably the MybTF protein has essentially the same biological activity as a MybTF protein encoded by SEQ ID NO: 2 or 6, preferably the MybTF protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and (iv) a nucleic acid encoding the same MybTF protein as the MybTF nucleic acids of (i) to (iii) above, but differing from the MybTF nucleic acids of (i) to (iii) above due to the degeneracy of the genetic code.

Preferably the MybTF nucleic acid is an isolated nucleic acid molecule comprising a nucleic acid selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3 or 4, or a functional fragment, derivative, orthologue, or paralogue thereof, or a splice variant thereof;

(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 5, or a functional fragment, derivative, orthologue, or paralogue thereof; preferably the MybTF protein has essentially the same biological activity as a MybTF protein encoded by SEQ ID NO: 3 or 4, preferably the MybTF protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and (iv) a nucleic acid encoding the same MybTF protein as the MybTF nucleic acids of (i) to (iii) above, but differing from the MybTF nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the MybTF nucleic acid is about 500-600, about 600-700, about 800-900, about 900-1000, about 1000-1100, about 1100-1200, about 1200-1300, or about 1300-1340 nucleotides, preferably consecutive nucleotides, preferably counted from the 5' or 3' end of the nucleic acid, in length, of the nucleic acid sequences given in SEQ ID NO: 2, 3, 1, 6, 4, 8, 9-24, 25, 27, 29, 31, 33, 35, 37, 39, 41, 43, 45, 47, 49, 51, 53, or 55.

Preferably, the MybTF nucleic acid comprises at least about 500, at least about 600, at least about 700, at least about 800, at least about 900, at least about 1100, at least about 1200, or at least about 1300 nucleotides, preferably continuous nucleotides, preferably counted from the 5' or 3' end of the nucleic acid or up to the full length of the nucleic acid sequence set out in SEQ ID NO: 2, 3, 1, 6, 4, 8, 9-24, 25, 27, 29, 31, 33, 35, 37, 39, 41, 43, 45, 47, 49, 51, 53, or 55.

Preferably, the MybTF nucleic acid comprises at least about 500, at least about 550, at least about 600, at least about 650, at least about 700, at least about 750, at least about 800, at least about 850, or at least about 900 nucleotides, preferably continuous nucleotides, preferably counted from the 5' or 3' end of the nucleic acid or up to the full length of the nucleic acid sequence set out in SEQ ID NO: 2, 3, 1, 6, 4, 9-24, 25, 27, 29, 31, 33, 35, 37, 39, 41, 43, 45, 47, 49, 51, 53, or 55.

Preferably the portion of the MybTF nucleic acid is about 500-550, about 550-600, about 600-650, about 650-700, about 675-708, about 700-750, about 750-800, about 800-850, about 850-900, or about 900-918 nucleotides, preferably consecutive nucleotides, preferably counted from the 5' or 3' end of the nucleic acid, in length, of the nucleic acid sequences given in SEQ ID NO: 2, 3, 1, 6, 4, 9-24, 25, 27, 29, 31, 33, 35, 37, 39, 41, 43, 45, 47, 49, 51, 53, or 55.

Preferably, the MybTF nucleic acid comprises at least about 500, at least about 550, at least about 600, at least about 650, at least about 700, at least about 750, at least about 800, at least about 850, or at least about 900 nucleotides, preferably continuous nucleotides, preferably counted from the 5' or 3' end of the nucleic acid or up to the full length of the nucleic acid sequence set out in SEQ ID NO: 2 or 3.

Preferably the portion of the MybTF nucleic acid is about 500-550, about 550-600, about 600-650, about 650-700, about 675-708, about 700-750, about 750-800, about 800-850, about 850-900, or about 900-918 nucleotides, preferably consecutive nucleotides, preferably counted from the 5' or 3' end of the nucleic acid, in length, of the nucleic acid sequences given in SEQ ID NO: 2 or 3.

Preferably, the MybTF nucleic acid is a MybTF nucleic acid splice variant. Preferred splice variants are splice variants of a nucleic acid represented by SEQ ID NO: 1 or 8. Preferred MybTF nucleic acids being a splice variant of SEQ ID NO: 1 or 8 are shown in FIG. 3.

Preferably, the MybTF nucleic acid is an isolated nucleic acid molecule comprising a splice variant of SEQ ID NO: 1 or 8, wherein the splice variant is selected from the group consisting of:

(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4 or 6, or a functional fragment, derivative, orthologue, or paralogue thereof;
(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7 or 5, or a functional fragment, derivative, orthologue, or paralogue thereof; preferably the MybTF protein has essentially the same biological activity as a MybTF protein encoded by SEQ ID NO: 1, 6, or 4; preferably the MybTF protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and
(iv) a nucleic acid encoding the same MybTF protein as the MybTF nucleic acids of (i) to (iii) above, but differing from the MybTF nucleic acids of (i) to (iii) above due to the degeneracy of the genetic code.

Preferred splice variants of SEQ ID NO: 1 or 8 consist of or comprise anyone of the nucleotide sequences shown in SEQ ID NO: 4 or 6. Most preferred is the MybTF nucleic acid splice variant as shown in SEQ ID NO: 6.

Preferably the MybTF nucleic acid is an isolated nucleic acid molecule comprising a nucleic acid selected from the group consisting of:
(i) a nucleic acid having in increasing order of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 8, or a splice variant thereof;
(ii) a nucleic acid molecule which hybridizes with a complementary sequence of any of the nucleic acid molecules of (i) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and
(iii) a nucleic acid encoding the same MybTF protein as the MybTF nucleic acids of (i) to (ii) above, but differing from the MybTF nucleic acids of (i) to (ii) above due to the degeneracy of the genetic code;
wherein the splice variant thereof is selected from the group consisting of:
(i) a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4 or 6, or a functional fragment, derivative, orthologue, or paralogue thereof;
(ii) a nucleic acid encoding a MybTF protein having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7 or 5, or a functional fragment, derivative, orthologue, or paralogue thereof; preferably the MybTF protein has essentially the same biological activity as a MybTF protein encoded by SEQ ID NO: 1, 6, or 4; preferably the MybTF protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and
(iv) a nucleic acid encoding the same MybTF protein as the MybTF nucleic acids of (i) to (iii) above, but differing from the MybTF nucleic acids of (i) to (iii) above due to the degeneracy of the genetic code.

More preferably the MybTF nucleic acid is an isolated nucleic acid molecule comprising a nucleic acid selected from the group consisting of:
a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1 or 8, or a splice variant thereof; wherein the splice variant thereof is selected from the group consisting of:
a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4 or 6, preferably SEQ ID NO:4.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The MybTF nucleic acids described herein are useful in the constructs, methods, plants, harvestable parts and products of the invention.

MybTF Proteins

The MybTF protein is preferably of the R2R3-MYB family, preferably defined by SEQ ID NO: 7, 5, 26, 28, 30, 32, 34, 36, 38, 40, 42, 44, 46, 48, 50, 52, 54, or 56, or a fragment, homolog, derivative, orthologue or paralogue thereof. Preferably, the MybTF protein of the present invention is encoded by a nucleic acid, which has at least 70% sequence identity, at least 80%, at least 90%, at least 92%, at least 95%, at least 97%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof. More preferably, the MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, or is a functional fragment thereof, an orthologue or a paralogue thereof. Most preferred is at least 90 identity, at least 92%, at least 95%, at least 97% identity, more preferred is at least 98% or at least 99% identity with SEQ ID NO: 7, 5, 26, 28, 30, 32, 34, 36, 38, 40, 42, 44, 46, 48, 50, 52, 54, or 56.

More preferably, the MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 7 or is a functional fragment thereof, an orthologue or a paralogue thereof.

More preferably, the MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 5, or is a functional fragment thereof, an orthologue or a paralogue thereof.

The MybTF protein is preferably defined by SEQ ID NO: 7, 5, 26, 28, 30, 32, 34, 36, 38, 40, 42, 44, 46, 48, 50, 52, 54, or 56, or a fragment, homolog, derivative, orthologue or paralogue thereof. Preferably, the MybTF protein of the present invention is encoded by a nucleic acid, which has at least 70% sequence identity, at least 80%, at least 90%, at least 92%, at least 95%, at least 97%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof. More preferably, the MybTF protein of the present invention has at least 70% sequence identity, at least 80%, at least 90%, at least 92%, at least 95%, at least 97%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, or is a functional fragment thereof, an orthologue or a paralogue thereof. Most preferred is at least 92%, at least 95%, at least 97% identity, more preferred is at least 98% or at least 99% identity with SEQ ID NO: 7, 5, 26, 28, 30, 32, 34, 36, 38, 40, 42, 44, 46, 48, 50, 52, 54, or 56.

Preferably, the MybTF protein is a protein consisting of or comprising an amino acid sequence selected from the group consisting of:
(i) an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, 5, 26, 28, 30, 32, 34, 36, 38, 40, 42, 44, 46, 48, 50, 52, 54, or 56, or a functional fragment, derivative, orthologue, or paralogue thereof; preferably the MybTF protein has essentially the same biological activity as a MybTF protein encoded by SEQ ID NO: 2, 3, 1, 6, or 4; preferably the MybTF protein confers enhanced fungal resistance relative to control plants; or
(ii) an amino acid sequence encoded by a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 3, 1, 6, 4, 8, 9-24, 25, 27, 29, 31, 33, 35, 37, 39, 41, 43, 45, 47, 49, 51, 53, or 55, or a functional fragment, derivative, orthologue, or paralogue thereof, or a splice variant thereof; preferably the MybTF protein confers enhanced fungal resistance relative to control plants.

Preferably, the MybTF protein is a protein comprising an amino acid sequence selected from the group consisting of:
(i) an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, or a functional fragment, derivative, orthologue, or paralogue thereof; preferably the MybTF protein has essentially the same biological activity as a MybTF protein encoded by SEQ ID NO: 2, 6, or 1, preferably the MybTF protein confers enhanced fungal resistance relative to control plants; or
(ii) an amino acid sequence encoded by a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 6, 9-16, or 1, or a functional fragment, derivative, orthologue, or paralogue thereof, or a splice variant thereof; preferably the MybTF protein confers enhanced fungal resistance relative to control plants.

Preferably, the MybTF protein is a protein comprising an amino acid sequence selected from the group consisting of:
(i) an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 5, or a functional fragment, derivative, orthologue, or paralogue thereof; preferably the MybTF protein has essentially the same biological activity as a MybTF protein encoded by SEQ ID NO: 3, 4, or 1; preferably the MybTF protein confers enhanced fungal resistance relative to control plants; or
(ii) an amino acid sequence encoded by a nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, 4, 17-24, or 1, or a functional fragment, derivative, orthologue, or paralogue thereof, or a splice variant thereof; preferably the MybTF protein confers enhanced fungal resistance relative to control plants.

A preferred derivative of a MybTF protein is a MybTF protein consisting of or comprising an amino acid sequence selected from the group consisting of:

an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 7, 5, 26, 28, 30, 32, 34, 36, 38, 40, 42, 44, 46, 48, 50, 52, 54, or 56, wherein the non-identical amino acid residues are conservative amino acid substitutions, preferably as shown in Table 1, of the corresponding amino acid residue of SEQ ID NO: 7, 5, 26, 28, 30, 32, 34, 36, 38, 40, 42, 44, 46, 48, 50, 52, 54, or 56; preferably the MybTF protein has essentially the same biological activity as SEQ ID NO: 7 or 5, or as a MybTF protein encoded by SEQ ID NO: 2, 3, 1, 6, or 4, preferably the MybTF protein confers enhanced fungal resistance relative to control plants.

Preferably, the MybTF protein consists of or comprises an amino acid sequence represented by SEQ ID NO: 7, 5, 26, 28, 30, 32, 34, 36, 38, 40, 42, 44, 46, 48, 50, 52, 54, or 56 with one or more conservative amino acid substitutions, preferably as shown in Table 1, of the corresponding amino acid residues of SEQ ID NO: 7, 5, 26, 28, 30, 32, 34, 36, 38, 40, 42, 44, 46, 48, 50, 52, 54, or 56. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 amino acid residues of SEQ ID NO: 7, 5, 26, 28, 30, 32, 34, 36, 38, 40, 42, 44, 46, 48, 50, 52, 54, or 56 are conservative amino acid substitutions, preferably as shown in Table 1, of the corresponding amino acid residue of SEQ ID NO: 7, 5, 26, 28, 30, 32, 34, 36, 38, 40, 42, 44, 46, 48, 50, 52, 54, or 56.

More preferably, the MybTF protein consists of or comprises an amino acid sequence having at least 70%, at least 80%, at least 85%, at least 90%, at least 95%, at least 98% or at least 99% sequence identity with an amino acid sequence as represented by SEQ ID NO: 7, 5, 26, 28, 30, 32, 34, 36, 38, 40, 42, 44, 46, 48, 50, 52, 54, or 56, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, or at least 120 of the non-identical amino acid residues, or wherein 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 or even all of the nonidentical amino acid residues are conservative amino acid substitutions, preferably as shown in Table 1, of the corresponding amino acid residue of SEQ ID NO: 7, 5, 26, 28, 30, 32, 34, 36, 38, 40, 42, 44, 46, 48, 50, 52, 54, or 56.

Percentages of identity of a polypeptide or protein are indicated with reference to the entire amino acid sequence specifically disclosed herein.

Preferably, the MybTF protein comprises at least about 100, at least about 150, at least about 200, at least about 225, at least about 250, at least about 275, or at least about 300 amino acid residues, preferably continuous amino acid residues, preferably counted from the N-terminus or the C-terminus of the amino acid sequence, or up to the full length of the amino acid sequence set out in SEQ ID NO: 5, 42, 44, 46, 48, 50, 52, 54, or 56.

Preferably, the MybTF polypeptide comprises about 100-150, about 150-200, about 200-225, about 225-250, about 250-275, about 275-300, or about 300-305 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 5, 42, 44, 46, 48, 50, 52, 54, or 56.

Preferably, the MybTF protein comprises at least about 100, at least about 125, at least about 150, at least about 175, at least about 200, or at least about 225 amino acid residues, preferably continuous amino acid residues, preferably counted from the N-terminus or the C-terminus of the amino acid sequence, or up to the full length of the amino acid sequence set out in SEQ ID NO: 7, 26, 28, 30, 32, 34, 36, 38, or 40.

Preferably, the MybTF polypeptide comprises about 100-125, about 125-150, about 150-175, about 175-200, about 200-225, or about 225-233 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 7, 26, 28, 30, 32, 34, 36, 38, or 40.

The MybTF proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phacopsoracea, for example soy bean rust, in a plant, plant part, or plant cell by increasing the expression of a MybTF protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phacopsoraceae, preferably against fungal pathogens of the genus *Phacopsora*, most preferably against *Phakopsora pachyrhizi* and *Phakopsora meibomiae*, also known as soy bean rust in plants or plant cells, wherein in comparison to wild type plants, wild type plant parts, or wild type plant cells a MybTF protein is overexpressed.

The present invention further provides a method for increasing resistance to fungal pathogens of the genus *Phacopsora*, most preferably against *Phakopsora pachyrhizi* and *Phakopsora meibomiae*, also known as soy bean rust in plants or plant cells by overexpression of a MybTF protein.

In preferred embodiments, the protein amount and/or function of the MybTF protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the MybTF nucleic acid.

In one embodiment of the invention, the MybTF protein is encoded by a nucleic acid comprising
(i) an exogenous nucleic acid having at least 70%, for example at least 75%, more preferably at least 80%, for example at least 85%, even more preferably at least 90%, for example at least 95% or at least 96% or at least 97% or at least 98% most preferably 99% identity with SEQ ID NO: 2, 3, 1, 6, 4, 8, 9-24, 25, 27, 29, 31, 33, 35, 37, 39, 41, 43, 45, 47, 49, 51, 53, or 55, a functional fragment thereof, or an orthologue or a paralogue thereof, or a splice variant thereof; or by
(ii) an exogenous nucleic acid encoding a protein comprising an amino acid sequence having at least 70%, for example at least 75%, more preferably at least 80%, for example at least 85%, even more preferably at least 90%, for example at least 95% or at least 96% or at least 97% or at least 98% most preferably 99% homology with SEQ ID NO: 7, 5, 26, 28, 30, 32, 34, 36, 38, 40, 42, 44, 46, 48, 50, 52, 54, or 56, a functional fragment thereof, an orthologue or a paralogue thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; or by
(iv) an exogenous nucleic acid encoding the same MybTF protein as the nucleic acids of (i) to (iii) above, but differing from the nucleic acids of (i) to (iii) above due to the degeneracy of the genetic code.

A method for increasing fungal resistance, preferably resistance to Phacopsoracea, for example soy bean rust, in a plant, plant part, or plant cell, by increasing the expression of a MybTF protein or a functional fragment, orthologue, paralogue or homologue thereof, or a splice variant thereof, wherein the MybTF protein is encoded by a nucleic acid comprising
(i) an exogenous nucleic acid having at least 70% sequence identity, at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof, an orthologue or a paralogue thereof, or a splice variant thereof;
(ii) an exogenous nucleic acid encoding a protein comprising an amino acid sequence having at least 70% sequence identity, at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code;
is a further embodiment of the invention.

A method for increasing fungal resistance, preferably resistance to Phacopsoracea, for example soy bean rust, in a plant, plant part, or plant cell, by increasing the expression of a MybTF protein or a functional fragment, orthologue, paralogue or homologue thereof, or a splice variant thereof, wherein the MybTF protein is encoded by
(i) an exogenous nucleic acid having at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;
(ii) an exogenous nucleic acid encoding a protein having at least 70% sequence identity, at least 80%, at least 90%, at least 95%, at least 98%, at least 99% sequence identity, or even 100% sequence identity with SEQ ID NO: 7 or 5, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phacopsoracea, for example soy bean rust, in a plant, plant part, or plant cell, by increasing the expression of a MybTF protein or a functional fragment, orthologue, paralogue or homologue thereof, or a splice variant thereof, wherein the MybTF protein is encoded by
(i) an exogenous nucleic acid having at least 70% sequence identity, at least 80%, at least 90%, at least 95%, at least 98%, at least 99% sequence identity, or even 100% sequence identity with SEQ ID NO: 2 or 6 or a functional fragment thereof, an orthologue or a paralogue thereof, or a splice variant thereof;
(ii) an exogenous nucleic acid encoding a protein having at least 70% sequence identity, at least 80%, at least 90%, at least 95%, at least 98%, at least 99% sequence identity, or even 100% sequence identity with SEQ ID NO: 7, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phacopsoracea, for example soy bean rust, in a plant, plant part, or plant cell, by increasing the expression of a MybTF protein or a functional fragment, orthologue, paralogue or homologue thereof, or a splice variant thereof, wherein the MybTF protein is encoded by
(i) an exogenous nucleic acid having at least 70% sequence identity, at least 80%, at least 90%, at least 95%, at least 98%, at least 99% sequence identity, or even 100% sequence identity with SEQ ID NO: 3 or 4 or a functional fragment thereof, an orthologue or a paralogue thereof, or a splice variant thereof;
(ii) an exogenous nucleic acid encoding a protein having at least 70% sequence identity, at least 80%, at least 90%, at least 95%, at least 98%, at least 99% sequence identity, or even 100% sequence identity with SEQ ID NO: 5, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code is a further embodiment of the invention.

In a further method of the invention, the method comprises the steps of
(a) stably transforming a plant cell with a recombinant expression cassette comprising
 (i) a nucleic acid having at least 70% sequence identity, at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof, or an orthologue or a paralogue thereof, or a splice variant thereof;
 (ii) a nucleic acid coding for a protein comprising an amino acid sequence having at least 70% sequence identity, at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
 (iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
 (iv) a nucleic acid encoding the same MybTF polypeptide as the nucleic acids of (i) to (iii) above, but differing from the nucleic acids of (i) to (iii) above due to the degeneracy of the genetic code,
in functional linkage with a promoter;
(b) regenerating the plant from the plant cell; and
(c) expressing said nucleic acid, optionally wherein the nucleic acid which codes for a MybTF protein is expressed in an amount and for a period sufficient to generate or to increase soybean rust resistance in said plant.

Preferably, the method comprises the steps of
(a) stably transforming a plant cell with a recombinant expression cassette comprising
 (i) a nucleic acid having at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
 (ii) a nucleic acid coding for a protein having at least 70% sequence identity, at least 80%, at least 90%, at least 95%, at least 98%, at least 99% sequence identity, or even 100% sequence identity with SEQ ID NO: 7 or 5, a functional fragment thereof, an orthologue or a paralogue thereof; preferably the encoded protein confers enhanced fungal resistance relative to control plants;
 (iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or (iv) a nucleic acid encoding the same MybTF polypeptide as the nucleic acids of (i) to (iii) above, but differing from the nucleic acids of (i) to (iii) above due to the degeneracy of the genetic code, in functional linkage with a promoter;

(b) regenerating the plant from the plant cell; and
(c) expressing said nucleic acid, optionally wherein the nucleic acid which codes for a MybTF protein is expressed in an amount and for a period sufficient to generate or to increase soybean rust resistance in said plant.

Preferably, the method comprises the steps of
(a) stably transforming a plant cell with a recombinant expression cassette comprising
   (i) a nucleic acid having at least 70% sequence identity, at least 80%, at least 90%, at least 95%, at least 98%, at least 99% sequence identity, or even 100% sequence identity with SEQ ID NO: 2 or 6, or a functional fragment thereof, or an orthologue or a paralogue thereof, or a splice variant thereof;
   (ii) a nucleic acid coding for a protein having at least 70% sequence identity, at least 80%, at least 90%, at least 95%, at least 98%, at least 99% sequence identity, or even 100% sequence identity with SEQ ID NO: 7, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and/or
   (iv) a nucleic acid encoding the same MybTF polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for a MybTF protein is expressed in an amount and for a period sufficient to generate or to increase soybean rust resistance in said plant.

Preferably, the method comprises the steps of
(a) stably transforming a plant cell with a recombinant expression cassette comprising
   (i) a nucleic acid having at least 70% sequence identity, at least 80%, at least 90%, at least 95%, at least 98%, at least 99% sequence identity, or even 100% sequence identity with SEQ ID NO: 3 or 4, or a functional fragment thereof, or an orthologue or a paralogue thereof, or a splice variant thereof;
   (ii) a nucleic acid coding for a protein having at least 70% sequence identity, at least 80%, at least 90%, at least 95%, at least 98%, at least 99% sequence identity, or even 100% sequence identity with SEQ ID NO: 5, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and/or
   (iv) a nucleic acid encoding the same MybTF polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for a MybTF protein is expressed in an amount and for a period sufficient to generate or to increase soybean rust resistance in said plant.

Preferably, the promoter is a rust induced and/or mesophyll-specific promoter, preferably the rust induced mesophyll specific promoter 820.

Preferably, the method for increasing fungal resistance, preferably resistance to Phacopsoracea, for example soy bean rust, in a plant, plant part, or plant cell further comprises the step of selecting a transgenic plant expressing
(i) an exogenous nucleic acid having at least 70% sequence identity, at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof, or an orthologue or a paralogue thereof, or a splice variant thereof;
(ii) an exogenous nucleic acid coding for a protein having at least 70% sequence identity, at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
(iii) an exogenous nucleic acid capable of hybridizing under stringent conditions a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
(iv) an exogenous nucleic acid encoding the same MybTF polypeptide as the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of a MybTF protein, wherein the MybTF protein is encoded by a nucleic acid comprising
(i) an exogenous nucleic acid having at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by (iv) an exogenous nucleic acid encoding the same MybTF protein as the nucleic acids of (i) to (iii) above, but differing from the nucleic acids of (i) to (iii) above due to the degeneracy of the genetic code, wherein increasing the expression of the MybTF protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of a MybTF protein, wherein the MybTF protein is encoded by a nucleic acid comprising (i) an exogenous nucleic acid having at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56; preferably the encoded protein confers enhanced fungal resistance relative to control plants; or (iii) an exogenous nucleic acid encoding the same MybTF protein as the nucleic acids of (i) to (ii) above, but differing from the nucleic acids of (i) to (ii) above due to the degeneracy of the genetic code, wherein increasing the expression of the MybTF protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 3

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight Anthracnose stalk rot | *Colletotrichum graminicola* (teleomorph: *Glomerella graminicola* Politis); *Glomerella tucumanensis* (anamorph: *Glomerella falcatum* Went) |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| Diplodia leaf spot or streak | *Stenocarpella macrospora* = *Diplodialeaf macrospora* |
| Brown stripe downy mildew | *Sclerophthora rayssiae* var. zeae |
| Crazy top downy mildew | *Sclerophthora macrospora* = *Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |
| Rostratum | *Setosphaeria rostrata*, (anamorph: |

TABLE 3-continued Diseases caused by necrotrophic and/or hemibiotrophic fungi and Oomycetes

| Disease | Pathogen |
|---|---|
| leaf spot (Helminthosporium leaf disease, ear and stalk rot) | xserohilum rostratum = Helminthosporium rostratum) |
| Java downy mildew | Peronosclerospora maydis = Sclerospora maydis |
| Philippine downy mildew | Peronosclerospora philippinensis = Sclerospora philippinensis |
| Sorghum downy mildew | Peronosclerospora sorghi = Sclerospora sorghi |
| Spontaneum downy mildew | Peronosclerospora spontanea = Sclerospora spontanea |
| Sugarcane downy mildew | Peronosclerospora sacchari = Sclerospora sacchari |
| Sclerotium ear rot (southern blight) | Sclerotium rolfsii Sacc. (teleomorph: Athelia rolfsii) |
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae (anamorph: F. graminearum), Macrophomina phaseolina, Penicillium spp., Phomopsis sp., Pythium spp., Rhizoctonia solani, R. zeae, Sclerotium rolfsii, Spicaria sp. |
| Selenophoma leaf spot | Selenophoma sp. |
| Yellow leaf blight | Ascochyta ischaemi, Phyllosticta maydis (teleomorph: Mycosphaerella zeae-maydis) |
| Zonate leaf spot | Gloeocercospora sorghi |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), Sclerophthora macrospora (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as Microdochium *nivale* (snow mold of rye and wheat), *Fusarium*, *Fusarium graminearum*, *Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea*, *Pyrenophora graminea* (leaf stripe of barley), *Pyrenophora teres* (net blotch of barley), *Pyrenophora tritici*-repentis (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (typhula blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum*, *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, more preferably heminecrotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales (rust), previously known as Uredinales, among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia*, *Gymnosporangium*, *Juniperus*, *Cronartium*, *Hemileia*, and *Uromyces*; preferably *Puccinia sorghi*, *Gymnosporangium juniperi-virginianae*, *Juniperus virginiana*, *Cronartium ribicola*, *Hemlleia vastatrix*, *Puccinia graminis*, *Puccinia coronata*, *Uromyces phaseoli*, *Puccinia hemerocallidis*, *Puccinia persistens* subsp. *Triticina*, *Puccinia striiformis*, *Puccinia graminis causes*, and/or *Uromyces appendeculatus*.

Further preferred pathogens, preferably pathogens of maize, are pathogens causing stalk rot diseases, in particular *Fusarium* stalk rot, *Gibberella* stalk rot, *Diplodia* stalk rot, and Charcoal rot and pathogens causing anthracnose. Preferred pathogens causing *Fusarium* stalk rot are *Fusarium verticillioides*, *Fusarium proliferatum* or *Fusarium subglutinans*. A preferred pathogen causing *Gibberella* stalk rot is *Fusarium graminearum*. A preferred pathogen causing *Diplodia* stalk rot is *Diplodia maydis*. A preferred pathogen causing Charcoal rot is *Macrophomina phaseollna*. A preferred pathogen causing anthracnose is *Colletotrichum graminicola*.

MybTF Expression Constructs and Vector Constructs

A recombinant vector construct comprising:
(a) (i) a nucleic acid having at least 70% sequence identity, at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof, or an orthologue or a paralogue thereof, or a splice variant thereof;
(ii) a nucleic acid coding for a protein comprising an amino acid sequence having at least 70% sequence identity, at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
(iv) a nucleic acid encoding the same MybTF protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55;
(ii) a nucleic acid coding for a protein comprising an amino acid sequence having at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
(iv) a nucleic acid encoding the same MybTF protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 1,
(ii) a nucleic acid coding for a protein having at least 80%, at least 90%, at least 95%, at least 98%, at least 99% sequence identity, or even 100% sequence identity with SEQ ID NO: 7 or 5; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
(iv) a nucleic acid encoding the same MybTF protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 2 or 6;
(ii) a nucleic acid coding for a protein having at least 80%, at least 90%, at least 95%, at least 98%, at least 99% sequence identity, or even 100% sequence identity with SEQ ID NO: 7; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and/or
(iv) a nucleic acid encoding the same MybTF protein as the nucleic acids of (i) to (iii) above, but differing from the nucleic acids of (i) to (iii) above due to the degeneracy of the genetic code,
operably linked with
(b) a promoter and
(c) a transcription termination sequence is a further embodiment of the invention.

Furthermore, a recombinant vector construct is provided comprising:
(a) (i) a nucleic acid having at least 80%, at least 90%, at least 95%, at least 98%, at least 99% sequence identity, or even 100% sequence identity with SEQ ID NO: 3 or 4;
(ii) a nucleic acid coding for a protein having at least 80%, at least 90%, at least 95%, at least 98%, at least 99% sequence identity, or even 100% sequence identity with SEQ ID NO: 5; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and/or (iv) a nucleic acid encoding the same MybTF protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

In the case of a genomic library, the natural genetic environment of the nucleic acid sequence is preferably retained, at least in part. The environment preferably flanks the nucleic acid sequence at least on one side and has a sequence length of at least 50 bp, preferably at least 500 bp, especially preferably at least 1000 bp, most preferably at least 5000 bp.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

In preferred embodiments, the increase in the protein amount and/or activity of the MybTF protein takes place in a constitutive or tissue-specific manner. In especially preferred embodiments, an essentially pathogen-induced increase in the protein amount and/or protein activity takes place, for example by recombinant expression of the MybTF nucleic acid under the control of a fungal-inducable promoter. In particular, the expression of the MybTF nucleic acid takes place on fungal infected sites, where, however, preferably the expression of the MybTF nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruitpreferred, ovule-preferred, male tissue-preferred, seed-preferred, integument-preferred, tuber-preferred, stalk-preferred, pericarp-preferred, leaf-preferred, stigma-preferred, pollenpreferred, anther-preferred, a petal-preferred, sepal-preferred, pedicel-preferred, siliquepreferred, stem-preferred, root-preferred promoters and/or the like. Seed preferred promoters are preferentially expressed during seed development and/or germination. For example, seed preferred promoters can be embryo-preferred, endosperm preferred and seed coatpreferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosinpromoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the 3-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-spezifisch promoters may be selected from the group consisting of: WIR5 (=GstA1); acc. X56012; Dudler & Schweizer, GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999); Prx7, acc. AJ003141, Kristensen B. K., Ammitzboll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von
- Wettstein D., Plant Phys Biochem 38, 685 (2000);
- OsROC1, acc. AP004656

RTBV, acc. AAV62708, AAV62707; Kloti A., Henrich C., Bieri S., He X., Chen G., Burkhardt P. K., Wünn J., Lucca P., Hohn T., Potrykus I. and Futterer J., PMB 40, 249 (1999); Chitinase ChtC2-Promoter from potato (Ancillo et al., Planta. 217(4), 566, (2003));

AtProT3 Promoter (Grallath et al., Plant Physiology. 137(1), 117 (2005)); SHN-Promoters from *Arabidopsis* (AP2/EREBP transcription factors involved in cutin and wax production) (Aaron et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:
- PPCZm1 (=PEPC); Kausch A. P., Owen T. P., Zachwieja S. J., Flynn A. R. and Sheen J., Plant Mol. Biol. 45, 1 (2001);
- OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993); OsPPDK, acc. AC099041;
- TaGF-2.8, acc. M63223; Schweizer P., Christoffel A. and Dudler R., Plant J. 20, 541 (1999);
- TaFBPase, acc. X53957;
- TaWIS1, acc. AF467542; US 200220115849;
- HvBIS1, acc. AF467539; US 200220115849;
- ZmMIS1, acc. AF467514; US 200220115849;
- HvPR1a, acc. X74939; Bryngelsson et al., Mol. Plant Microbe Interacti. 7 (2), 267 (1994);
- HvPR1b, acc. X74940; Bryngelsson et al., Mol. Plant Microbe Interact. 7(2), 267 (1994);
- HvB1,3gluc; acc. AF479647;
- HvPrx8, acc. AJ276227; Kristensen et al., Molecular Plant Pathology, 2(6), 311 (2001); and/or
- HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
- PcUbi promoter from parsley (WO 03/102198)
- CaMV 35S promoter: Cauliflower Mosaic Virus 35S promoter (Benfey et al. 1989 EMBO J. 8(8): 2195-2202),
- STPT promoter: *Arabidopsis thaliana* Short Triose phosphate translocator promoter (Accession NM_123979)
- Act1 promoter: *Oryza sativa* actin 1 gene promoter (McElroy et al. 1990 PLANT CELL 2(2) 163-171 a) and/or
- EF1A2 promoter: *Glycine max* translation elongation factor EF1 alpha (US 20090133159).

In preferred embodiments, the increase in the protein quantity or function of the MybTF protein takes place in a constitutive or tissue-specific manner. In especially preferred embodiments, an essentially pathogen-induced increase in the protein quantity or protein function takes place, for example by exogenous expression of the MybTF nucleic acid under the control of a fungal-inducible promoter, preferably a rust-inducible promoter. In particular, the expression of the MybTF nucleic acid takes place on fungal infected sites, where, however, preferably the expression of the MybTF nucleic acid sequence remains essentially unchanged in tissues not infected by fungus.

Preferably, the MybTF nucleic acid is under the control of a rust induced mesophyll specific promoter. More preferably, the promoter is the rust induced mesophyll specific promoter 820.

A preferred terminator is the terminator of the cathepsin D inhibitor gene from *Solanum tuberosum*.

Preferred promoter-terminator combinations with the gene of interest inbetween are a promoter from parsley, preferably, the parsley ubiquitine promoter, in combination with the terminator of the cathepsin D inhibitor gene from *Solanum tuberosum*. Another preferred promoter-terminator combination is the rust induced mesophyll specific promoter 820 in combination with the terminator of the cathepsin D inhibitor gene from *Solanum tuberosum*.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

One type of vector construct is a "plasmid," which refers to a circular double stranded DNA loop into which additional DNA segments can be ligated. Another type of vector is a viral vector, wherein additional DNA segments can be ligated into the viral genome. Certain vecfor constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous MybTF protein, preferably the transgenic plant comprises a recombinant expression construct encoding the MybTF protein. Preferably, the MybTF protein overexpressed in the plant, plant part or plant cell is encoded by a nucleic acid comprising (i) an exogenous nucleic acid having at least 70% identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment, thereof, an orthologue or a paralogue thereof, or a splice variant thereof; or by (ii) an exogenous nucleic acid encoding a protein comprising an amino acid sequence having at least 70% identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55; or comprises an exogenous nucleic acid encoding a protein having at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56.

A preferred embodiment is a transgenic plant, transgenic plant part, or transgenic plant cell overexpressing an exogenous MybTF protein. Preferably, the MybTF protein overexpressed in the plant, plant part or plant cell is encoded by
(i) an exogenous nucleic acid having at least 70% identity with SEQ ID NO: 1 or a functional fragment, thereof, an orthologue or a paralogue thereof, or a splice variant thereof; or by
(ii) an exogenous nucleic acid encoding a protein having at least 70% identity with SEQ ID NO: 7 or 5, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous MybTF protein. Preferably, the MybTF protein overexpressed in the plant, plant part or plant cell is encoded by
(i) an exogenous nucleic acid having at least 70% identity with SEQ ID NO: 2 or 6 or a functional fragment, thereof, an orthologue or a paralogue thereof, or a splice variant thereof; or by
(ii) an exogenous nucleic acid encoding a protein having at least 70% identity with SEQ ID NO: 7, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous MybTF protein. Preferably, the MybTF protein overexpressed in the plant, plant part or plant cell is encoded by
(i) an exogenous nucleic acid having at least 70% identity with SEQ ID NO: 3 or 4 or a functional fragment, thereof, an orthologue or a paralogue thereof, or a splice variant thereof; or by
(ii) an exogenous nucleic acid encoding a protein having at least 70% identity with SEQ ID NO: 5, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and/or by
(iv) an exogenous nucleic acid encoding the same MybTF protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 7 or 5.

Most preferably, the exogenous nucleic acid has at least 80%, at least 90%, at least 95%, at least 98%, at least 99% sequence identity, or even 100% sequence identity with SEQ ID NO: 2 or 6; or comprises an exogenous nucleic acid encoding a protein having at least 80%, at least 90%, at least 95%, at least 98%, at least 99% sequence identity, or even 100% sequence identity with SEQ ID NO: 7.

Most preferably, the exogenous nucleic acid has at least 80%, at least 90%, at least 95%, at least 98%, at least 99% sequence identity, or even 100% sequence identity with SEQ ID NO: 3 or 4; or comprises an exogenous nucleic acid encoding a protein having at least 80%, at least 90%, at least 95%, at least 98%, at least 99% sequence identity, or even 100% sequence identity with SEQ ID NO: 5.

In preferred embodiments, the protein amount of a MybTF protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the MybTF nucleic acid.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Hofgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the MybTF nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomice*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, arabidopsis, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. *axiphium* Alef emend. C.O. Lehm), also called snow pea, edible-podded pea or mangetout, (*Pisum granda sneida* L. convar. *sneidulo* p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to a MybTF nucleic acid, which is preferably SEQ ID NO: 2, 3, 6, 4, or 1, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step (c) expressing the MybTF protein, preferably encoded by a nucleic acid comprising
   (i) an exogenous nucleic acid having at least 70% identity with SEQ ID NO: 2, 3, 1, 6, 4, 8, 9-24, 25, 27, 29, 31, 33, 35, 37, 39, 41, 43, 45, 47, 49, 51, 53, or 55, a functional fragment thereof, an orthologue or a paralogue thereof, or a splice variant thereof;
   (ii) an exogenous nucleic acid encoding a protein comprising an amino acid sequence having at least 70% identity with SEQ ID NO: 7, 5, 26, 28, 30, 32, 34, 36, 38, 40, 42, 44, 46, 48, 50, 52, 54, or 56, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
   (iv) an exogenous nucleic acid encoding the same MybTF protein as the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step (c) expressing the MybTF protein, preferably encoded by
   (i) an exogenous nucleic acid having at least 70% identity with SEQ ID NO: 1, a functional fragment thereof, an orthologue or a paralogue thereof, or a splice variant thereof;
   (ii) an exogenous nucleic acid encoding a protein having at least 70% identity with SEQ ID NO: 7 or 5, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
   (iv) an exogenous nucleic acid encoding the same MybTF protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step (c) expressing the MybTF protein, preferably encoded by
  (i) an exogenous nucleic acid having at least 70% identity with SEQ ID NO: 2 or 6, a functional fragment thereof, an orthologue or a paralogue thereof, or a splice variant thereof;
  (ii) an exogenous nucleic acid encoding a protein having at least 70% identity with SEQ ID NO: 7, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7; preferably the encoded protein confers enhanced fungal resistance relative to control plants; and/or by
  (iv) an exogenous nucleic acid encoding the same MybTF protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step (c) expressing the MybTF protein, preferably encoded by
  (i) an exogenous nucleic acid having at least 70% identity with SEQ ID NO: 3 or 4, a functional fragment thereof, an orthologue or a paralogue thereof, or a splice variant thereof;
  (ii) an exogenous nucleic acid encoding a protein having at least 70% identity with SEQ ID NO: 5, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 5; preferably the encoded protein confers enhanced fungal resistance relative to control plants; and/or by
  (iv) an exogenous nucleic acid encoding the same MybTF protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing
  (i) an exogenous nucleic acid having at least 70% sequence identity, at least 80%, at least 90%, at least 95%, at least 98%, at least 99% sequence identity, or even 100% sequence identity with SEQ ID NO: 2, 3, 1, 6, 4, 8, 9-24, 25, 27, 29, 31, 33, 35, 37, 39, 41, 43, 45, 47, 49, 51, 53, or 55, or a functional fragment thereof, or an orthologue or a paralogue thereof, or a splice variant thereof;
  (ii) an exogenous nucleic acid coding for a protein having at least 70% sequence identity, at least 80%, at least 90%, at least 95%, at least 98%, at least 99% sequence identity, or even 100% sequence identity with SEQ ID NO: 7, 5, 26, 28, 30, 32, 34, 36, 38, 40, 42, 44, 46, 48, 50, 52, 54, or 56, a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
  (iv) an exogenous nucleic acid encoding the same MybTF polypeptide as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
  (i) the exogenous nucleic acid having at least 70% identity with SEQ ID NO: 2, 3, 1, 6, 4, 8, 9-24, 25, 27, 29, 31, 33, 35, 37, 39, 41, 43, 45, 47, 49, 51, 53, or 55, a functional fragment thereof, an orthologue or a paralogue thereof, or a splice variant thereof;
  (ii) the exogenous nucleic acid encoding a protein comprising an amino acid sequence having at least 70% identity with SEQ ID NO: 7, 5, 26, 28, 30, 32, 34, 36, 38, 40, 42, 44, 46, 48, 50, 52, 54, or 56, or a functional fragment thereof, an orthologue or a paralogue thereof; preferably the encoded protein confers enhanced fungal resistance relative to control plants;
  (iii) the exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or
  (iv) the exogenous nucleic acid encoding the same MybTF protein as the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises
  (i) the exogenous nucleic acid having at least 70% identity with SEQ ID NO: 2, 3, 1, 6, 4, 8, 9-24, 25, 27, 29, 31, 33, 35, 37, 39, 41, 43, 45, 47, 49, 51, 53, or 55, a functional fragment thereof, an orthologue or a paralogue thereof, or a splice variant thereof;
  (ii) the exogenous nucleic acid encoding a protein comprising an amino acid sequence having at least 70% identity with SEQ ID NO: 7, 5, 26, 28, 30, 32, 34, 36, 38, 40, 42, 44, 46, 48, 50, 52, 54, or 56, or a functional fragment thereof, an orthologue or a paralogue thereof; preferably the encoded protein confers enhanced fungal resistance relative to control plants;
  (iii) the exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or (iv) the exogenous nucleic acid encoding the same MybTF protein as the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the MybTF gene or by directly screening for the MybTF nucleic acid).

Furthermore, the use of the exogenous MybTF nucleic acid or the recombinant vector construct comprising the MybTF nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the MybTF nucleic acid or MybTF protein. The harvestable parts may be seeds, roots, leaves and/or flowers comprising the MybTF nucleic acid or MybTF protein or parts thereof. Preferred parts of soy plants are soy beans comprising the MybTF nucleic acid or MybTF protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the MybTF nucleic acid or MybTF protein.

Preferably the harvestable parts of the transgenic plant according to the present invention or the products derived from a transgenic plant comprise an exogenous nucleic acid molecule consisting of or comprising a nucleic acid selected from the group consisting of:

(i) an exogenous nucleic acid having in increasing order of preference at least at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 3, 1, 6, 4, 8, 9-24, 25, 27, 29, 31, 33, 35, 37, 39, 41, 43, 45, 47, 49, 51, 53, or 55, or a functional fragment, derivative, orthologue, or paralogue thereof, or a splice variant thereof;

(ii) an exogenous nucleic acid encoding a MybTF protein comprising an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, 5, 26, 28, 30, 32, 34, 36, 38, 40, 42, 44, 46, 48, 50, 52, 54, or 56, or a functional fragment, derivative, orthologue, or paralogue thereof; preferably the MybTF protein has essentially the same biological activity as a MybTF protein encoded by SEQ ID NO: 1, 2, 4, or 6; preferably the MybTF protein confers enhanced fungal resistance relative to control plants;

(iii) an exogenous nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and (iv) an exogenous nucleic acid encoding the same MybTF protein as the MybTF nucleic acids of (i) to (iii) above, but differing from the MybTF nucleic acids of (i) to (iii) above due to the degeneracy of the genetic code, or wherein the harvestable part of the transgenic plant or the product derived from the transgenic plant comprises a MybTF protein encoded by any one of the MybTF nucleic acids of (i) to (iv).

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) an exogenous nucleic acid having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 2, 3, 1, 6, 4, 8, 9-24, 25, 27, 29, 31, 33, 35, 37, 39, 41, 43, 45, 47, 49, 51, 53, or 55, or a functional fragment, derivative, orthologue, or paralogue thereof, or a splice variant thereof;

(ii) an exogenous nucleic acid encoding a MybTF protein comprising an amino acid sequence having in increasing order of preference at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 7, 5, 26, 28, 30, 32, 34, 36, 38, 40, 42, 44, 46, 48, 50, 52, 54, or 56, or a functional fragment, derivative, orthologue, or paralogue thereof; preferably the MybTF protein has essentially the same biological activity as a MybTF protein encoded by SEQ ID NO: 1, 2, 4, or 6; preferably the MybTF protein confers enhanced fungal resistance relative to control plants;

(iii) an exogenous nucleic acid molecule which hybridizes with a complementary sequence of any of the nucleic acid molecules of (i) or (ii) under high stringency hybridization conditions; preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and (iv) an exogenous nucleic acid encoding the same MybTF protein as the MybTF nucleic acids of (i) to (iii) above, but differing from the MybTF nucleic acids of (i) to (iii) above due to the degeneracy of the genetic code, or wherein the product obtained by said method comprises a MybTF protein encoded by any one of the MybTF nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the MybTF nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a MybTF protein, preferably encoded by a nucleic acid comprising
  (i) an exogenous nucleic acid having at least 70% identity with SEQ ID NO: 2, 3, 1, 6, 4, 8, 9-24, 25, 27, 29, 31, 33, 35, 37, 39, 41, 43, 45, 47, 49, 51, 53, or 55, a functional fragment thereof, an orthologue or a paralogue thereof, or a splice variant thereof;
  (ii) an exogenous nucleic acid encoding a protein comprising an amino acid sequence having at least 70% identity with SEQ ID NO: 7, 5, 26, 28, 30, 32, 34, 36, 38, 40, 42, 44, 46, 48, 50, 52, 54, or 56, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a MybTF protein; preferably wherein the nucleic acid molecule codes for a polypeptide which has essentially identical properties to the polypeptide described in SEQ ID NO: 7 or 5; preferably the encoded protein confers enhanced fungal resistance relative to control plants; and/or by
  (iv) an exogenous nucleic acid encoding the same MybTF protein as the nucleic acids of (i) to (iii) above, but differing from the nucleic acids of (i) to (iii) above due to the degeneracy of the genetic code.

Another preferred embodiment is a method for plant improvement comprising (a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the MybTF protein; and optionally
(f) producing propagation material from the plants expressing the nucleic acid encoding the MybTF protein.

The transgenic plants may be selected by known methods as described above (e.g., by screening for the presence of one or more markers which are encoded by plant-expressible genes co-transferred with the MybTF gene or screening for the MybTF nucleic acid itself).

According to the present invention, the introduced MybTF nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous MybTF nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The genomic DNA sequence and the optimized cDNAs of the MybTF gene mentioned in this application were generated by DNA synthesis (Geneart, Regensburg, Germany).

The MybTF DNA (as shown in SEQ ID NO: 1) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, Calif., USA) in a way that the full-length fragment is located in sense direction between the parsley ubiquitin promoter and the *Agrobacterium tumefaciens* derived octopine synthase terminator (t-OCS). The PcUbi promoter regulates constitutive expression of the ubi4-2 gene (accession number X64345) of Petroselinum crispum (Kawalleck et al. 1993 Plant Molecular Biology 21(4): 673-684).

Figure 2:
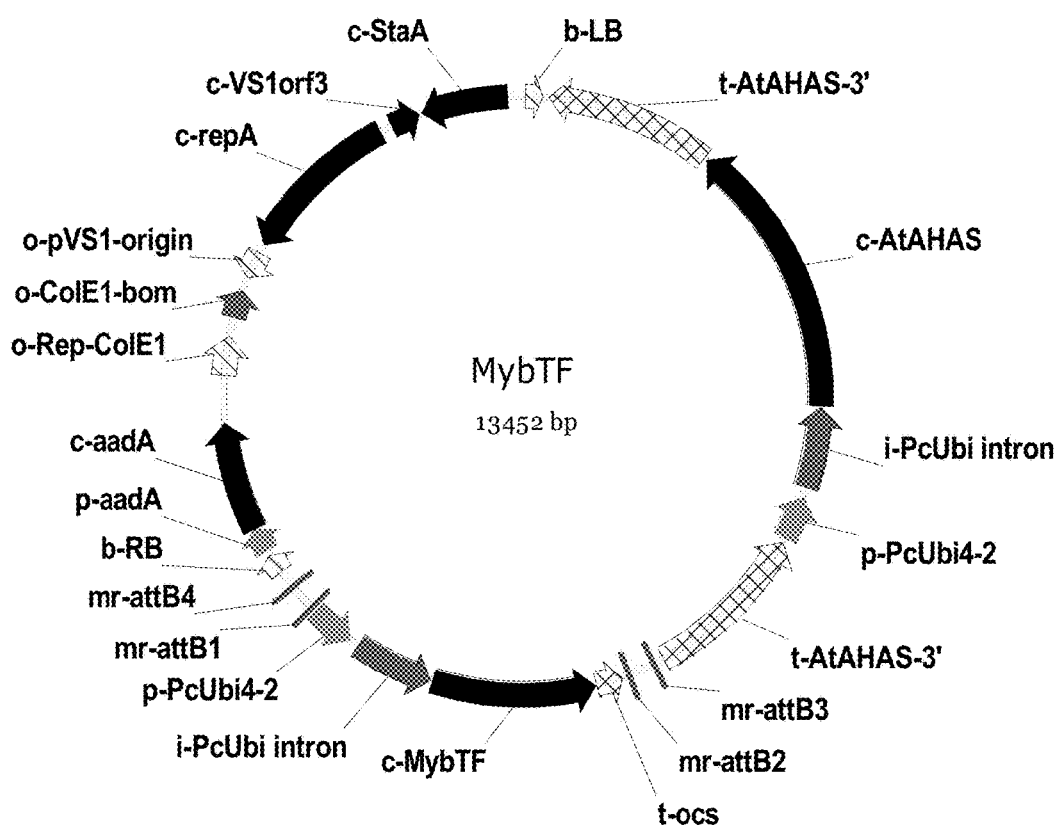

To obtain the binary plant transformation vector, a triple LR reaction (Gateway system, Invitrogen, Life Technologies, Carlsbad, Calif., USA) was performed according to manufacturer's protocol by using an empty pENTRY-A vector, the PcUbi promoter::MybTF::OCSterminator in the above described pENTRY-B vector and an empty pENTRY-C. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a PcUbi-promoter (see FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For Method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud.

These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD600 between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the OD600 was between 0.8 and 1.0. Before preparing the soy explants, the Agrobacteria were pelleted by centrifugation for 10 min at 5,500×g at 20° C. The pellet was resuspended in liquid CCM to the desired density (OD600 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed.

Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol. Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 μE/m$^2$s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after cocultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day- and 8 h-night-Rhythm at a temperature of 16 and 22° C. and a humidity of 75%) till the first 2 trifoliate leaves were fully expanded.

4.2 Inoculation

The plants were inoculated with spores of *P. pachyrhizi.*

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×10$^5$ spores/ml. For the microscopy, a density of >5×10$^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution 11 (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 15 T0 soybean plants expressing MybTF protein were inoculated with spores of *Phakopsora pachyrhizi*. The macroscopic disease symptoms of soy against *P. pachyrhizi* of the inoculated soybean plants were scored 14 days after inoculation.

The average of the percentage of the leaf area showing fungal colonies or strong yellowing/browning on all leaves was considered as diseased leaf area. At all 15 soybean To plants expressing MybTF (expression checked by RT-PCR) were evaluated in parallel to non-transgenic control plants. Non-transgenic soy plants grown in parallel to the transgenic plants were used as control. The average of the diseased leaf area is shown in FIG. 4 for plants expressing recombinant MybTF protein compared with wildtype plants. Overexpression of the MybTF reduces the diseased leaf area in comparison to non-transgenic control plants by 72.3% in average over all events and plants generated. This data clearly indicates that the in-planta expression of the MybTF expression vector construct (see FIG. 2) lead to a lower disease scoring of transgenic plants compared to non-transgenic controls. So, the expression of MybTF nucleic acid (as shown in SEQ ID NO: 1) in soybean significantly ($p<0.001$) increases the resistance of soy against soybean rust.

Example 7: Construction of Maize Expression Cassettes

The nucleic acid sequence encoding the optimized cDNAs of MYB-TF (as shown in SEQ ID NO:2 and SEQ ID NO:3) were synthesized in a way that an AscI restriction site is located in front of the start-ATG and a PstI restriction site downstream of the stop-codon. The synthesized cDNAs were digested using the restriction enzymes AscI and PstI (NEB Biolabs) and ligated in an AscI/PstI digested binary plant transformation vector (description see below) in a way that the full-length Myb-TF cDNA is located in sense direction downstream of a SCBV254 promoter (Sugarcane Bacilliform Virus promoter fragment ScBV-254) and upstream of a t-nos terminator (3'UTR of Nopaline Synthase from *Agrobacterium tumefaciens*). An intron from the rice Met1 gene was also cloned in between of the promoter and the Myb-TF cDNA sequences.

As backbone a binary plant transformation vector was used, which is composed of: (1) a Kanamycin resistance cassette for bacterial selection (2) a pVS1 origin for replication in Agrobacteria (3) a ColE1 origin of replication for stable maintenance in *E. coli* and (4) between the right and left border a ZmAHAS gene as selectable marker under control of a ZmAHAS-promoter. A comprehensive description of the components of a binary plant transformation vector can be found in the literature. Examples for plant binary vectors are pBi-nAR (Hofgen & Willmitzer 1990, Plant Sci. 66:221-230), pSUN300 or pSUN2-GW vectors and the pPZP vectors (Hajdukiewicz et al., Plant Molecular Biology 25: 989-994, 1994).

The recombinant binary plant transformation vectors containing the Myb-TF cDNA expression cassettes were transformed into Top10 cells (Invitrogen) using standard conditions. Transformed cells were selected on LB agar containing 50 µg/ml kanamycin grown overnight at 37° C. Plasmid DNA was extracted using the QIAprep Spin Miniprep Kit (Qiagen) following manufacturer's instructions. Analysis of subsequent clones and restriction mapping was performed according to standard molecular biology techniques (Sambrook et al., 1989, "Molecular Cloning: A Laboratory Manual," 2nd Edition, Cold Spring Harbor Laboratory Press, Cold Spring Harbor, N.Y.).

Example 8: Maize Transformation

*Agrobacterium* cells harboring a plasmid containing the gene of interest (see above) and the mutated maize AHAS gene were grown in YP medium supplemented with appropriate antibiotics for 1-2 days. One loop of *Agrobacterium* cells was collected and suspended in 1.8 ml M-LS-002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591, 616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing cocultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 µM imazethapyr and grown for three weeks at 27° C. to select for transformed callus cells.

Plant regeneration was initiated by transferring resistant calli to M-LS-504 medium supplemented with 0.75 µM imazethapyr and growing under light at 26° C. for two to three weeks. Regenerated shoots were then transferred to a rooting box with M-MS-618 medium (0.5 µM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety. Transformation of maize may be made using *Agrobacterium* transformation, as described in U.S. Pat. Nos. 5,591,616; 5,731,179; U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription. Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

Example 9: *Fusarium* and *Colletotrichum* Resistance Screening

Transgenic maize plants expressing the Myb-TF cDNAs (SEQ ID NO:2 and SEQ ID NO:3), under control of the constitutive SCBV254 promoter (Sugarcane Bacilliform Virus promoter fragment ScBV-254), were grown in greenhouse or phyto-chamber under standard growing conditions in a controlled environment (20-25° C., 60-90% humidity).

Shortly after the transgenic maize plants enter the reproductive phase they are inoculated near the base of the stalk using a fungal suspension of spores ($10^5$ spores in PBS solution) of *Fusarium* ssp. or *Colletotrichum graminicola*. Plants are incubated for 2-4 weeks at 20-25° C. and 60-90% humidity.

For scoring the stalk rot disease, stalks are split and the progression of the disease is scored by observation of the characteristic brown to black color of the fungus as it grows up the stalk. Disease ratings are conducted by assigning a visual score. Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines The expression of the Myb-TF gene will lead to enhanced resistance of corn against *Fusarium* ssp. and *Colletotrichum graminicola*.

The invention claimed is:

1. A method for increasing soybean rust resistance in a soybean plant, a soybean plant part, or a soybean plant cell, said method comprising transforming a soybean plant, soybean plant part, or soybean plant cell with an exogenous nucleic acid encoding a Myeloblastosis-like transcription factor (MybTF) protein comprising an amino acid sequence with at least 85% identity to SEQ ID NO:7, wherein the MybTF protein confers increased resistance against soybean rust thereto in comparison to a wild type soybean plant, wild type soybean plant part or wild type soybean plant cell.

2. The method of claim 1, comprising (a) stably transforming a soybean plant cell with an expression cassette comprising an exogenous nucleic acid encoding a protein having an amino acid sequence with at least 85% identity with SEQ ID NO: 7 in functional linkage with a promoter; and (b) regenerating the soybean plant from the soybean plant cell.

3. The method of claim 2, wherein the promoter is a constitutive promoter, pathogen-inducible promoter, a mesophyll-specific promoter or an epidermis specific-promoter.

4. A transgenic soybean plant, transgenic soybean plant part, or transgenic soybean plant cell comprising an exogenous nucleic acid encoding a MybTF protein having an amino acid sequence with at least 85% identity with SEQ ID NO: 7, wherein the MybTF protein confers increased resistance against soybean rust thereto in comparison to a wild type soybean plant, wild type soybean plant part or wild type soybean plant cell.

5. A method for the production of a transgenic soybean plant, transgenic soybean plant part, or transgenic soybean plant cell having increased resistance against soybean rust, comprising (a) introducing a recombinant vector construct into a soybean plant, a soybean plant part, or a soybean plant cell, wherein the recombinant vector construct comprises:

(i) a nucleic acid encoding a MybTF protein having an amino acid sequence with at least 85% identity with SEQ ID NO: 7, operably linked with (ii) a heterologous promoter, and (iii) a transcription termination sequence; and (b) generating a transgenic soybean plant, transgenic soybean plant part, or transgenic soybean plant cell from the soybean plant, soybean plant part or soybean plant cell, wherein expression of said recombinant vector construct in the transgenic soybean plant, transgenic soybean plant part, or transgenic soybean plant cell confers increased resistance against soybean rust thereto in comparison to a wild type soybean plant, wild type soybean plant part, or wild type soybean plant cell.

6. The method of claim 5, further comprising the step of harvesting the seeds of the transgenic soybean plant and planting the seeds and growing the seeds to soybean plants, wherein the grown soybean plants comprise the exogenous nucleic acid encoding a protein having an amino acid sequence with at least 85% identity with SEQ ID NO: 7.

7. A harvestable part of the transgenic soybean plant of claim 4, wherein the part comprises the exogenous nucleic acid encoding a protein having an amino acid sequence with at least 85% identity with SEQ ID NO: 7.

8. A product derived from the transgenic soybean plant of claim 4, wherein the product comprises the exogenous nucleic acid encoding a protein having an amino acid sequence with at least 85% identity with SEQ ID NO: 7.

9. A method for the production of a product comprising a) growing the soybean plant of claim 4; and b) producing said product from or by the plant and/or part of the plant.

10. The method of claim 9 comprising a) growing the soybean plant and removing the harvestable parts from the plant; and b) producing said product from or by the harvestable parts of the plant.

11. The method of claim 9, wherein the product is meal or oil.

12. The method of claim 1, wherein the resistance against soybean rust is resistance against *Phakopsora meibomiae* and/or *Phakopsora pachyrhizi*.

13. A method for breeding a fungal resistant soybean plant comprising (a) crossing the soybean plant of claim 4 with a second soybean plant;

(b) obtaining seed from the cross of step (a);

(c) planting said seeds and growing the seeds to soybean plants; and (d) selecting from the soybean plants produced in step (c) plants expressing the MybTF protein.

14. A method for controlling soybean rust in a soybean plant, said method comprising providing a transgenic soybean plant comprising a nucleic acid encoding a MybTF protein having an amino acid sequence with at least 85% identity to SEQ ID NO: 7, wherein expression of the nucleic acid leads to increased soybean rust resistance in said soybean plant as compared to a wild type soybean plant such that soybean rust is controlled in the transgenic soybean plant.

15. The method of claim 14, wherein the soybean rust that is controlled is *Phakopsora meibomiae* and/or *Phakopsora pachyrhizi*.

16. The method of claim 1, wherein the MybTF protein comprises an amino acid sequence with at least 95% identity to SEQ ID NO:7.

17. The method of claim 1, wherein the MybTF protein comprises an amino acid sequence with at least 90% identity to SEQ ID NO:7.

18. The method of claim 14, wherein the MybTF protein has an amino acid sequence with at least 95% identity to SEQ ID NO:7.

19. The method of claim 14, wherein the MybTF protein has an amino acid sequence with at least 90% identity to SEQ ID NO:7.

20. The transgenic soybean plant, transgenic soybean plant part, or transgenic soybean plant cell of claim 4, wherein the MybTF protein has an amino acid sequence with at least 95% identity to SEQ ID NO:7.

21. The transgenic soybean plant, transgenic soybean plant part, or transgenic soybean plant cell of claim 4, wherein the MybTF protein has an amino acid sequence with at least 90% identity to SEQ ID NO:7.

* * * * *